US012788365B2

(12) United States Patent
Matthias

(10) Patent No.: US 12,788,365 B2
(45) Date of Patent: Nov. 10, 2026

(54) TECHNOLOGIES FOR ULTRASOUND ASYNCHRONOUS RESONANCE IMAGING (ARI) FOR NEEDLE TIP LOCALIZATION

(71) Applicant: EASTERN SONOGRAPHICS CORPORATION, Philadelphia, PA (US)

(72) Inventor: Isaac Matthias, Philadelphia, PA (US)

(73) Assignee: EASTERN SONOGRAPHICS CORPORATION

( * ) Notice: Subject to any disclaimer, the term of this patent is extended or adjusted under 35 U.S.C. 154(b) by 0 days.

(21) Appl. No.: 19/672,187

(22) Filed: May 8, 2026

(65) Prior Publication Data

US 2026/0263041 A1 Sep. 10, 2026

Related U.S. Application Data

(63) Continuation of application No. 18/717,735, filed as application No. PCT/US2022/052586 on Dec. 12, 2022, now Pat. No. 12,635,981.

(60) Provisional application No. 63/288,072, filed on Dec. 10, 2021, provisional application No. 63/293,322, filed on Dec. 23, 2021, provisional application No.
(Continued)

(51) Int. Cl.
*A61B 8/00* (2006.01)
*A61B 8/08* (2006.01)

(52) U.S. Cl.
CPC .......... *A61B 8/4461* (2013.01); *A61B 8/0841* (2013.01); *A61B 8/461* (2013.01)

(58) Field of Classification Search
CPC ..... A61B 8/4461; A61B 8/0841; A61B 8/461; A61B 8/4477; A61B 8/48; A61B 8/5207; A61B 8/5238; A61B 8/5253; A61B 8/54; A61B 8/5269
See application file for complete search history.

(56) References Cited

U.S. PATENT DOCUMENTS 6,589,181 B2 * 7/2003 Grunwald ................ A61B 8/00 600/455
2003/0039171 A1 * 2/2003 Chiapetta ................ G01S 15/88 367/98
(Continued)

FOREIGN PATENT DOCUMENTS

CN 103315774 A 9/2013
DE 3311804 A1 10/1984
(Continued)

*Primary Examiner* — Amal Aly Farag
(74) *Attorney, Agent, or Firm* — The Belles Group, P.C.

(57) ABSTRACT

Technologies are disclosed for an ultrasound scanner that may perform a needle tip detection process that may include transmitting, at a first time, ultrasonic first pulse signals. The ultrasonic first pulse signals may be configured to cause first echo signals to be produced by adjacent tissue and a needle within the tissue. The scanner may receive, upon reaching a second time that is subsequent to the first time by a predetermined delay period, the first echo signals from the needle. The scanner may generate needle tip image data corresponding to a location of a tip of the needle based on the first echo signals. The scanner may perform a tissue detection process and/or may generate a compound image that includes a visual indicator of the location of the needle tip with respect to the tissue based on the needle tip image data and tissue image data.

20 Claims, 40 Drawing Sheets

Related U.S. Application Data

63/296,607, filed on Jan. 5, 2022, provisional application No. 63/299,558, filed on Jan. 14, 2022, provisional application No. 63/307,701, filed on Feb. 8, 2022, provisional application No. 63/318,986, filed on Mar. 11, 2022, provisional application No. 63/348,160, filed on Jun. 2, 2022.

(56) References Cited

U.S. PATENT DOCUMENTS

| | | | |
|---|---|---|---|
| 2004/0002653 | A1 | 1/2004 | Greppi et al. |
| 2006/0241451 | A1 | 10/2006 | Nakaya et al. |
| 2009/0149867 | A1 | 6/2009 | Glozman et al. |
| 2013/0274608 | A1 | 10/2013 | Takeda et al. |
| 2015/0094569 | A1 | 4/2015 | Ohuchi et al. |
| 2015/0272549 | A1 | 10/2015 | Samset et al. |
| 2016/0106392 | A1 | 4/2016 | Manbachi et al. |
| 2016/0206289 | A1 | 7/2016 | Yamamoto et al. |
| 2016/0302772 | A1* | 10/2016 | Cummins ............ A61B 8/4494 |
| 2017/0143295 | A1 | 5/2017 | Park et al. |
| 2020/0069330 | A1 | 3/2020 | Butki |
| 2020/0214678 | A1 | 7/2020 | Chiang et al. |

FOREIGN PATENT DOCUMENTS

| | | | |
|---|---|---|---|
| EP | 1281368 | A2 | 2/2003 |
| JP | 2006150069 | A | 6/2006 |
| JP | H11253445 | A | 1/2008 |
| JP | 2009173373 | A | 8/2009 |
| JP | 20130090746 | A | 4/2013 |
| JP | 2014200784 | A | 10/2014 |
| JP | 2017509429 | A | 4/2017 |
| WO | 2008020157 | A1 | 2/2008 |

* cited by examiner

TECHNOLOGIES FOR ULTRASOUND ASYNCHRONOUS RESONANCE IMAGING (ARI) FOR NEEDLE TIP LOCALIZATION

CROSS-REFERENCE TO RELATED APPLICATIONS

This U.S. Non-Provisional Patent Application is a Continuation of U.S. Non-Provisional application Ser. No. 18/717,735, filed Jun. 7, 2024, which is a U.S. National Stage Application under 35 U.S.C. § 371 of Patent Cooperation Treaty (PCT) Application No. PCT/US2022/052586, filed Dec. 12, 2022, which claims the benefit of U.S. Provisional Patent Application No. 63/288,072, filed Dec. 10, 2021; U.S. Provisional Patent Application No. 63/293,322, filed on Dec. 23, 2021; U.S. Provisional Patent Application No. 63/296,607, filed on Jan. 5, 2022; U.S. Provisional Patent Application No. 63/299,558, filed on Jan. 14, 2022; U.S. Provisional Patent Application No. 63/307,701, filed on Feb. 8, 2022; U.S. Provisional Patent Application No. 63/318,986, filed on Mar. 11, 2022; and U.S. Provisional Patent Application No. 63/348,160, filed on Jun. 2, 2022, the disclosures of all of which being hereby incorporated by reference herein in their respective entireties, for all purposes.

BACKGROUND

Medical ultrasound technologies may include medical imaging, diagnostic, and/or therapeutic techniques using ultrasound energy. Ultrasound energy may be used to create an image of internal body structures such as tendons, muscles, joints, blood vessels, and internal organs. Ultrasound energy may be used to monitor the gestation process. Ultrasound energy can be used to measure/image dynamic medical variables (e.g., blood flow, etc.). Medical ultrasound techniques may be referred to as medical ultrasonography and/or medical sonography.

Ultrasound energy emissions may be composed of sound waves (e.g., ultrasound waves) with frequencies which are higher than the those in the range of human hearing (e.g., greater than 20,000 Hz). Ultrasonic imaging is conducted by sending ultrasound energy (e.g., pulses thereof) into target tissue using one or more imaging probes. The ultrasound pulses may echo off of tissues, such as the target tissues, and may be received by the one or more imaging probes. The ultrasound echo energy/pulses/signals may have different reflection properties. Medical ultrasound devices may use the ultrasound echo signals for the imaging, diagnostic, or therapeutic processes.

SUMMARY

Technologies are disclosed for ultrasound scanner devices, and/or techniques performed thereby. The ultrasound scanner may have one or more imaging probes. One or more techniques may comprise performing a needle tip detection process. The needle tip detection process may comprise transmitting, at a first time, one or more ultrasonic first pulse signals. The one or more ultrasonic first pulse signals may be configured to cause one or more first echo signals to be produced by adjacent tissue and/or a needle within the tissue.

Techniques may comprise receiving, upon reaching a second time that is subsequent to the first time by a predetermined delay period, the one or more first echo signals from the needle. Techniques may comprise generating needle tip image data corresponding to a location of a tip of the needle based on the one or more first echo signals.

Techniques may comprise performing a tissue detection process. The tissue detection process may comprise transmitting one or more ultrasonic second pulse signals. The one or more ultrasonic second pulse signals may be configured to cause one or more second echo signals to be produced by the adjacent tissue and the needle within the tissue. Techniques may comprise receiving the one or more second echo signals from the adjacent tissue. Techniques may comprise generating tissue image data corresponding to the adjacent tissue based on the one or more second echo signals.

Techniques may comprise generating a compound image. The compound image may include a visual indicator of the location of the needle tip with respect to the tissue based on the needle tip image data and/or the tissue image data. Techniques may comprise displaying the compound image on a display.

Technologies are disclosed for one or more ultrasound scanner devices and/or one or more techniques performed thereby. One or more ultrasound scanner devices may comprise one or more imaging probes. One or more ultrasound scanner devices may comprise a display. One or more ultrasound scanner devices may comprise one or more processors. At least one processor may be configured to perform a needle tip detection process. The processor may be configured to transmit, at a first time, one or more ultrasonic first pulse signals. The one or more ultrasonic first pulse signals may be configured to cause one or more first echo signals to be produced by adjacent tissue and/or a needle within the tissue. The processor may be configured to receive, upon reaching a second time that is subsequent to the first time by a predetermined delay period, the one or more first echo signals from the needle. The processor may be configured to generate needle tip image data corresponding to a location of a tip of the needle based on the one or more first echo signals.

The processor may be configured to perform a tissue detection process. The processor may be configured to transmit one or more ultrasonic second pulse signals. The one or more ultrasonic second pulse signals may be configured to cause one or more second echo signals to be produced by the adjacent tissue and the needle within the tissue. The processor may be configured to receive the one or more second echo signals from the adjacent tissue. The processor may be configured to generate tissue image data corresponding to the adjacent tissue based on the one or more second echo signals.

The processor may be configured to generate a compound image that includes a visual indicator of the location of the needle tip with respect to the tissue based on the needle tip image data and the tissue image data. The processor may be configured to display the compound image on the display.

Technologies are disclosed for one or more ultrasound scanner devices and/or one or more techniques performed thereby. The ultrasound scanner(s) may have an imaging probe. One or more techniques may comprise performing a target object detection process. The target object detection process may comprise transmitting, at a first time, one or more ultrasonic first pulse signals. The one or more ultrasonic first pulse signals may be configured to cause one or more first echo signals to be produced by adjacent tissue and a target object within the tissue. Techniques may comprise receiving, upon reaching a second time that is subsequent to the first time by a predetermined delay period, the one or more first echo signals from the target object. Techniques may comprise generating target object image data corresponding to a location of the target object based on the one or more first echo signals.

Techniques may comprise performing a tissue detection process. The tissue detection process may comprise transmitting one or more ultrasonic second pulse signals. The one or more ultrasonic second pulse signals may be configured to cause one or more second echo signals to be produced by the adjacent tissue and the target object within the tissue. Techniques may comprise receiving the one or more second echo signals from the adjacent tissue. Techniques may comprise generating tissue image data corresponding to the adjacent tissue based on the one or more second echo signals.

Techniques may comprise generating a compound image that includes a visual indicator of the location of the target object with respect to the tissue based on the target object image data and the tissue image data. Techniques may comprise displaying the compound image on a display.

Technologies are disclosed for one or more ultrasound scanner devices and/or one or more techniques performed thereby. The ultrasound scanner may have one or more imaging probes. One or more techniques may comprise transmitting, at a first time, one or more ultrasonic pulse signals. The one or more ultrasonic pulse signals may be configured to cause one or more echo signals to be produced by adjacent tissue and a needle within the tissue.

Techniques may comprise performing a needle tip detection process. The needle tip detection process may comprise receiving, upon reaching a second time that is subsequent to the first time by a predetermined delay period, the one or more echo signals from the needle. Techniques may comprise generating needle tip image data corresponding to a location of a tip of the needle based on the one or more echo signals.

Techniques may comprise performing a tissue detection process. The tissue detection may comprise receiving the one or more echo signals from the adjacent tissue. Techniques may comprise generating tissue image data corresponding to the adjacent tissue based on the one or more echo signals.

Techniques may comprise generating a compound image that includes a visual indicator of the location of the needle tip with respect to the tissue based on the needle tip image data and the tissue image data. Techniques may comprise displaying the compound image on a display.

BRIEF DESCRIPTION OF DRAWINGS

The elements and other features, advantages and disclosures contained herein, and the manner of attaining them, will become apparent and the present disclosure will be better understood by reference to the following description of various examples of the present disclosure taken in conjunction with the accompanying drawings, wherein.

DETAILED DESCRIPTION

Figure 1:
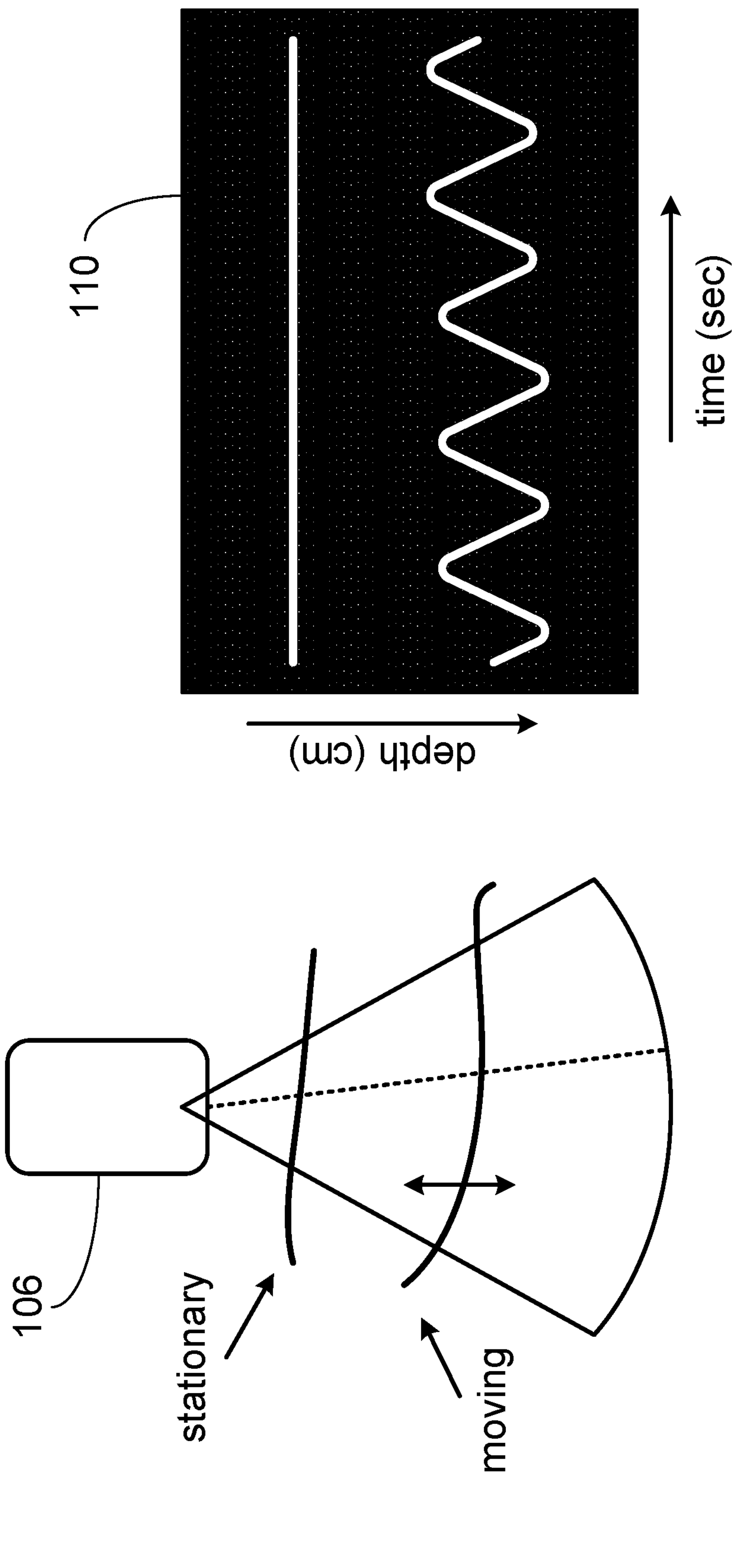
FIG. 1 is an example illustration of an M-mode ultrasound technique.

For the purposes of promoting an understanding of the principles of the present disclosure, reference will now be made to the examples illustrated in the drawings, and specific language will be used to describe the same. It will nevertheless be understood that no limitation of the scope of this disclosure is thereby intended.

A technique used to produce a standard ultrasound image may be referred to as "B-mode" (Brightness mode) imaging. This technique may produce a two-dimensional image of a subject's/patient's anatomy. At least two other imaging modes may be used in certain clinical areas, both of them are one-dimensional techniques.

A technique such as "M-mode" (Motion mode) may be used in echocardiography to provide detailed information regarding the movements of the subject's/patient's heart walls and/or valves. To produce an M-mode display, an ultrasound scanner device may keep an ultrasound beam in a fixed position and (e.g., repeatedly) transmit and receive along this beam. The display of the echoes is swept slowly from left to right on the screen over a period of several seconds, for example.

Structures that are stationary relative to the probe (e.g., the subject's/patient's chest wall) may be displayed at a constant depth and therefore as horizontal lines. Structures that move towards and away from the probe (e.g., the heart walls) may move up and down the screen and so the display will document their position as a function of time, as shown in FIG. 1.

FIG. 1 is an example illustration of an M-mode ultrasound technique. In FIG. 1, an imaging probe/transmitter 106 may transmit a beam that is directed along the line of sight indicated by the broken line. At 110, the resulting M-mode display shows the depth of the tissue structure along this line of sight as a function of time over a period of several seconds, for example. The M-mode display may provide information about the amount of movement of individual structures, the speed at which they move, and their acceleration, for example.

Figure 2:
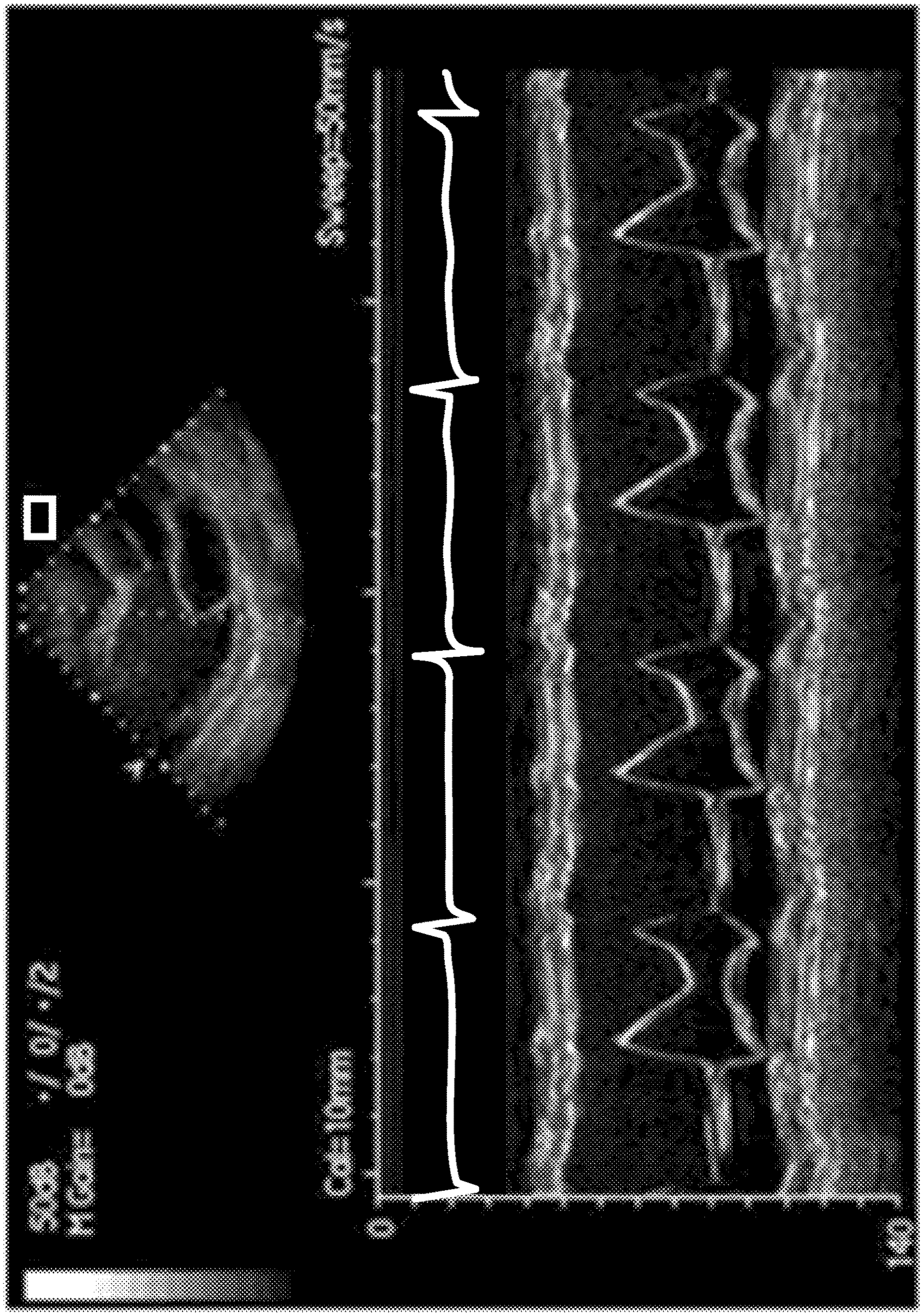
FIG. 2 is an example illustration of an M-mode trace showing the movement of the mitral valve leaflets.

FIG. 1 illustrates the relative position of structures and how that may change with time (e.g., the maximum and/or minimum diameters of a heart chamber, and/or the movement of two valve leaflets as the valve opens and closes). FIG. 2 is an example of an example electrocardiogram (ECG) trace that may be shown on the ultrasound image screen to provide a timing reference, for example. FIG. 2 is an example illustration of an M-mode trace showing the movement of the mitral valve leaflets.

Figure 3:
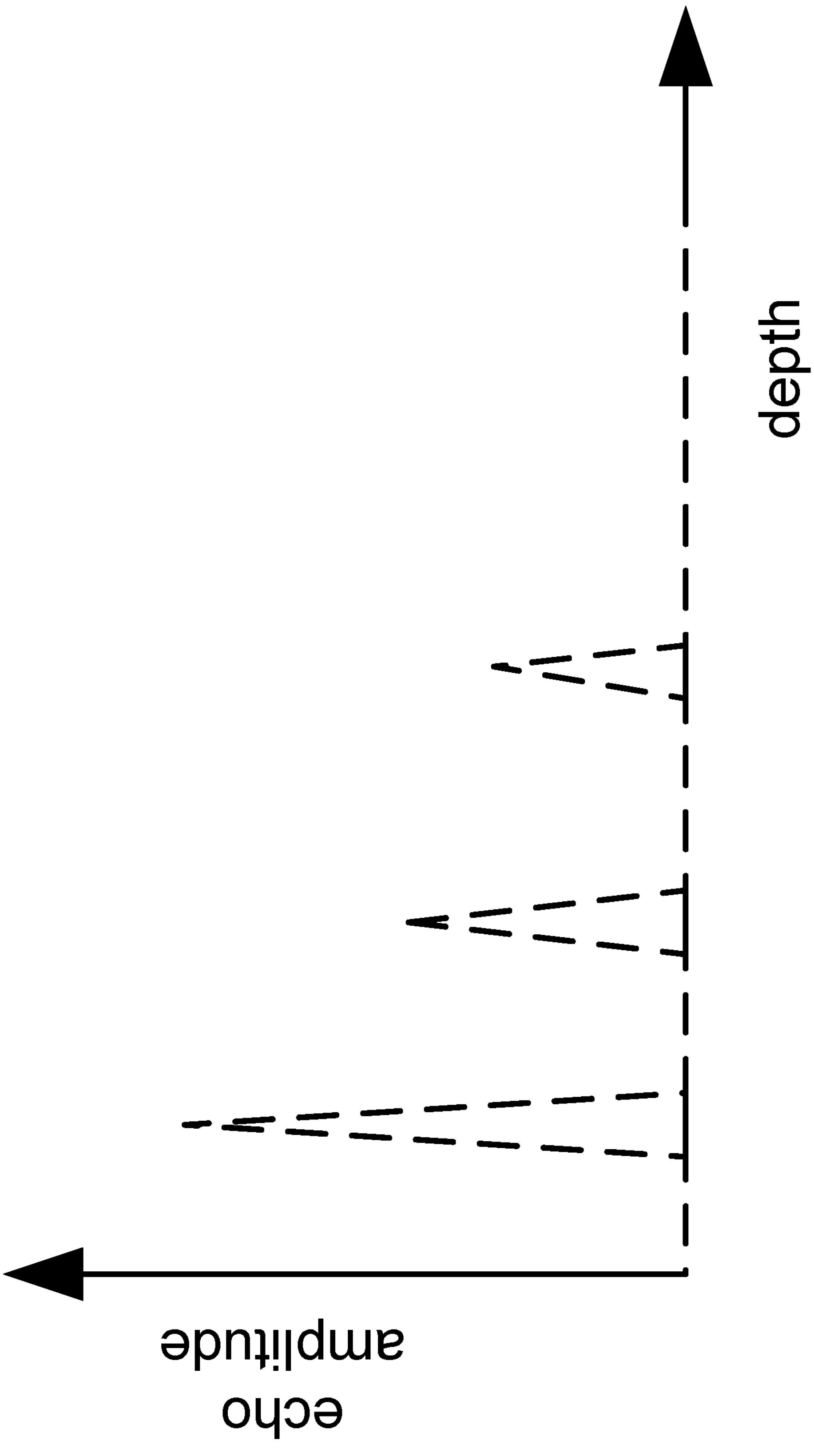
FIG. 3 illustrates an example display of an A-mode technique that may show echo amplitude as a function of depth.

Another one-dimensional imaging mode is the A-mode (e.g., Amplitude mode) display. The beam may be kept in a fixed position and the scanner/machine may transmit and receive along this line of sight. FIG. 3 illustrates an example display of an A-mode technique that may show echo amplitude as a function of depth. The A-mode display/technique may be useful in certain examinations, such as some eye scans, perhaps for example due to the ability to measure the depth of the various echoes accurately, among other reasons.

Figure 5:
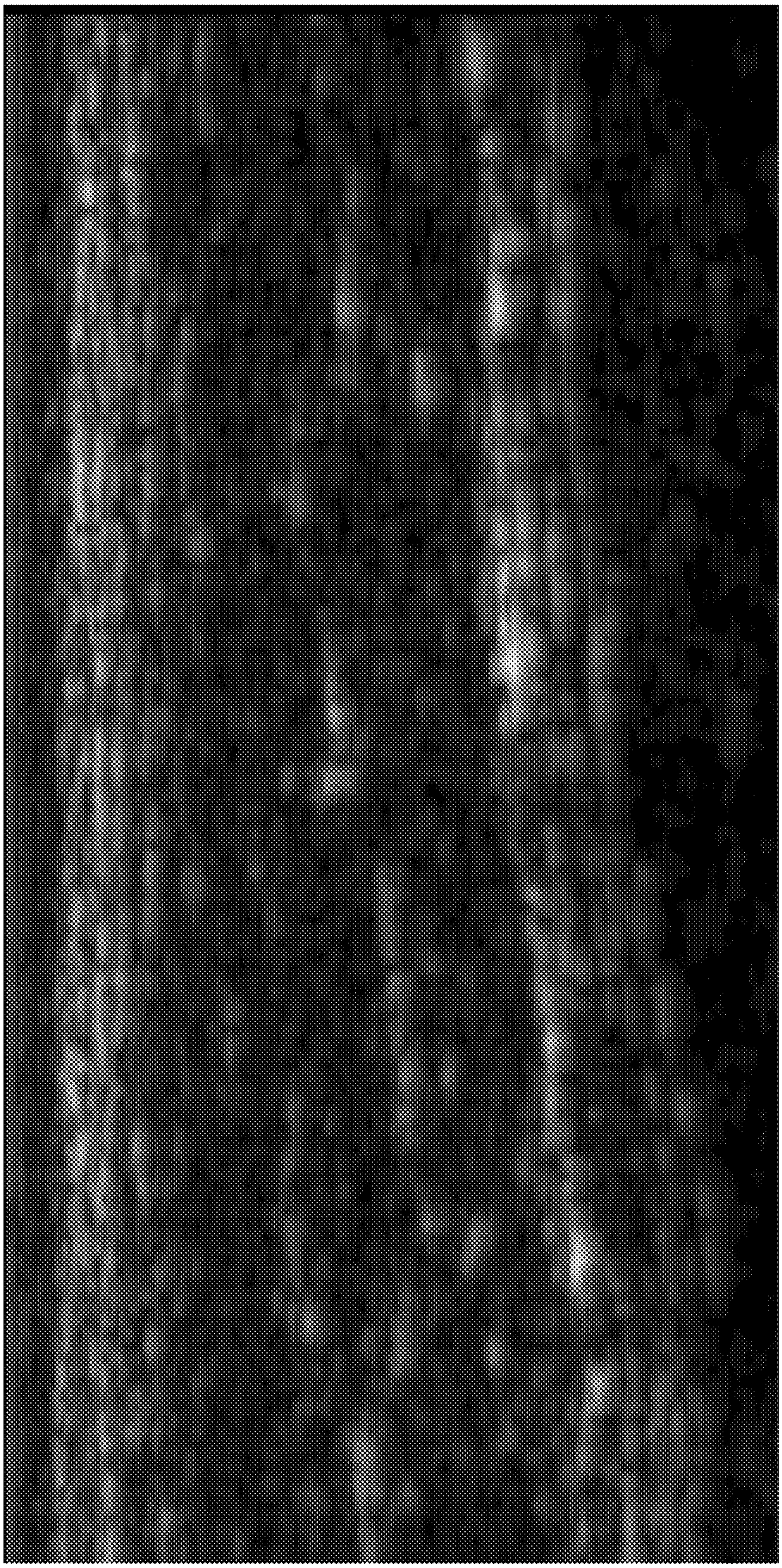
FIG. 5 illustrates an example of a B-mode ultrasound image with good soft tissue visualization but relatively poor needle tip conspicuity/visualization.

Referring again to the two-dimensional medical ultrasound technique, also known as "B-mode", this technique may be used to provide image guidance for the position of a needle tip in needle placement procedures. B-mode ultrasound provides (e.g., excellent) images of soft tissue structures, such as blood vessels. In one or more scenarios, B-mode may poorly visualize the tip of the needle. This causes a situation where the clinician can see the target blood vessel on the ultrasound image but cannot/might not effectively guide the needle tip to the target. FIG. 5 illustrates an example of a B-mode image with good soft tissue visualization but (e.g., relatively) poor needle tip conspicuity. The B-mode ultrasound image in FIG. 5 is of a pork belly phantom. A needle tip is present near the center of FIG. 5, but it is not easily distinguishable from other hyperechoic structures in the image.

Figure 6:
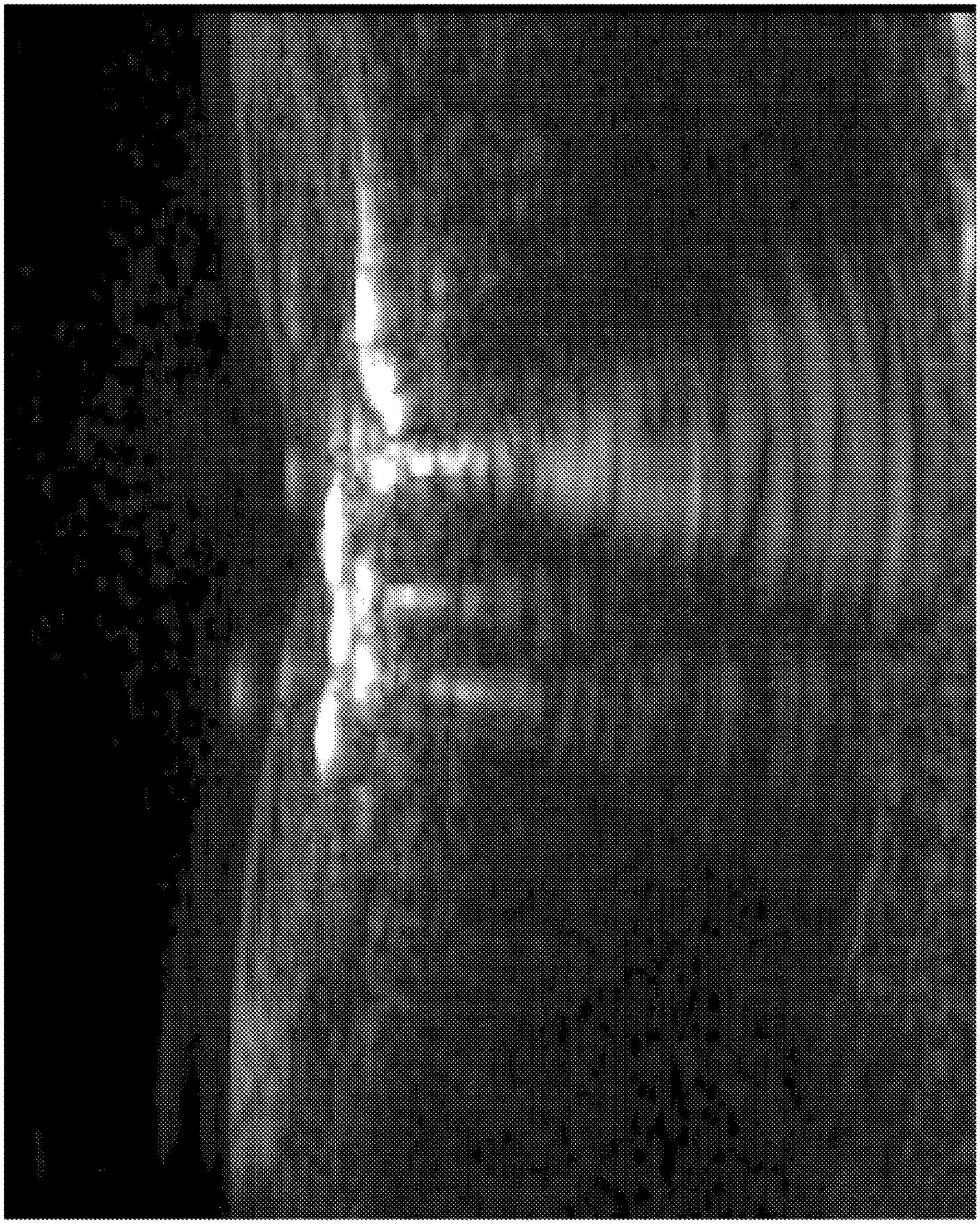
FIG. 6 illustrates an example of ringdown artifact(s) in an ultrasound image.

In one or more scenarios, a "ringdown" artifact in B-mode ultrasound may appear as a vertical line. The vertical line may (e.g., often) be composed of repeating short horizontal lines, starting at a given feature and proceeding to the bottom of the image screen. The short horizontal lines may sometimes spread laterally with increasing distance from the originating feature. FIG. 6 illustrates an example of ringdown artifact(s) in an ultrasound image with an image depth of 30 millimeters.

In FIG. 6, the ringdown artifact is seen in a lung ultrasound, where it may be referred to as "B-lines", originating from pathology at the lung/pleura interface. This can also be produced by metal objects, such as medical devices. Although a needle is composed of metal, the needle tip might not (e.g., typically) create a ringdown artifact.

In one or more scenarios, perhaps for a given feature in a B-mode ultrasound image, among other scenarios, the lateral position may be determined by the relative strength of echoes received by individual elements on an ultrasound transducer's one-dimensional array of elements, for example. The depth position may be determined by the amount of time that passes from when the transmitter/probe sends a pulse to when the probe/receiver may receive echoes from that feature/structure/tissue. The relationship of the depth position in the image to the time duration from transmitting a pulse to receiving an echo is known as the "pulse echo principle" in the art. In B-mode ultrasound, the echo receive period begins when the pulse is transmitted, and the amount of time that passes from when the pulse is transmitted to when one or more, or each, echo is received (e.g., that may be precisely recorded). This may enable recreation of an image with accurate depth of the included features.

In standard B-mode ultrasound, a needle tip may produce ringdown artifact echoes, but they may be obscured by stronger echoes from surrounding soft tissue. Due to these reasons, among others, the needle tip ringdown artifact might not be visualized.

As described herein, hereinafter referred to as asynchronous resonance imaging (ARI), ARI may use a time delay between when the ultrasound pulse is transmitted and when the echo receive period begins. For example, for an imaging depth of 20 millimeters, a time delay (e.g., typically of 40-500 microseconds and/or 100-400 microseconds) may be used. Once the time delay ends, the echo receive period begins. Again by way of example, for an imaging depth of 20 millimeters, the echo receive period may last approximately 26 microseconds given the soft tissue speed of sound constant of 1.54 millimeters per microsecond and the maximum depth round trip of 40 millimeters.

In one or more scenarios, the adjustment of the (e.g., predetermined) delay period might not change the depth of the narrowest portion of the double ringdown artifact as displayed by the compound image.

In one or more scenarios, the longest delay period where needle tip double ringdown artifact echoes may still be present may be in the range of 160-500 microseconds. In one or more scenarios, for example with a very long/powerful pulse and/or a special needle, double ringdown artifact echoes may be present after longer delay periods.

In one or more scenarios, the shortest delay period where tissue echoes are weak enough to be removed by signal processing, or may be absent, is in the range of 40-200 microseconds. For example, a needle tip in a tub of water produces no tissue echoes and standard B-mode imaging may show ringdown artifact(s), perhaps without double ringdown artifacts.

In one or more scenarios, the shorter the delay period, the stronger may be the needle tip echoes and/or the tissue echoes. A delay period that is (e.g., too) short may result in tissue echoes obscuring the needle tip double ringdown artifact. A delay period that is (e.g., too) long may result in a weak or absent double ringdown artifact. An optimal delay period that maximizes double ringdown artifact conspicuity may vary based on machine settings and patient factors. In one or more scenarios, the (e.g., predetermined, user/operator adjustable) delay period may be as short as possible without tissue echoes, for example.

During the time delay, soft tissue echoes dissipate. In one or more scenarios, ringdown artifact echoes from the needle tip may persist, as they are produced by resonance. A standard B-mode image reconstruction may be performed on the received echoes, assigning the beginning of the echo receive period to time zero (0), for example when the ultrasound pulse was transmitted. The needle tip double ringdown artifact may be visualized.

Figure 7:
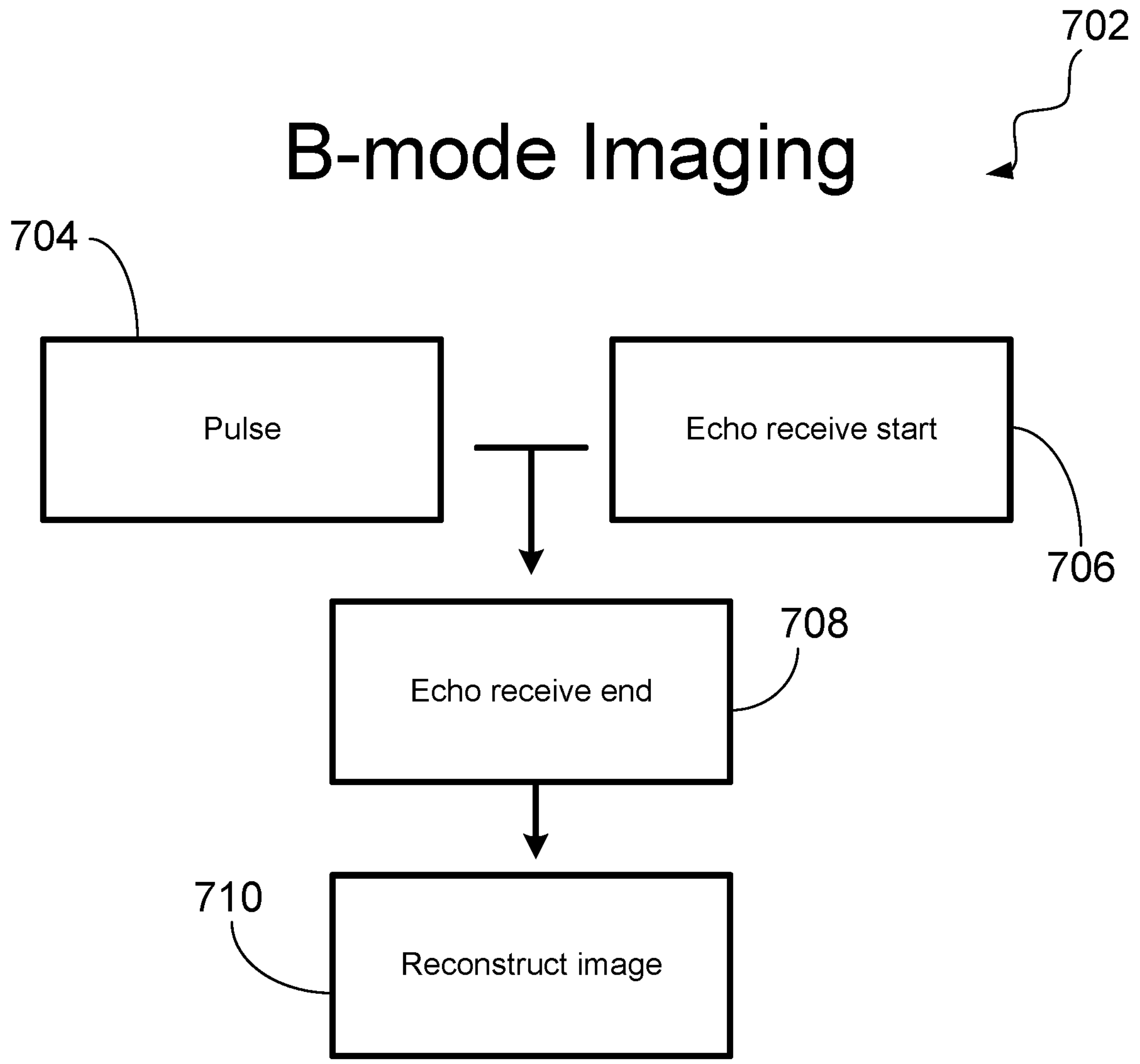
FIG. 7 illustrates a block diagram of an example imaging sequence for a B-mode technique.

FIG. 7 illustrates a block diagram of an example imaging sequence/technique 702 for a (e.g., standard) B-mode technique. At 704, at least one pulse may be generated into target tissue. At 706, one or more echo signals may be received. At 708, receipt of the one or more echo signals may end. At 710, the received echo signals may be used to construct/reconstruct an image.

Figure 8:
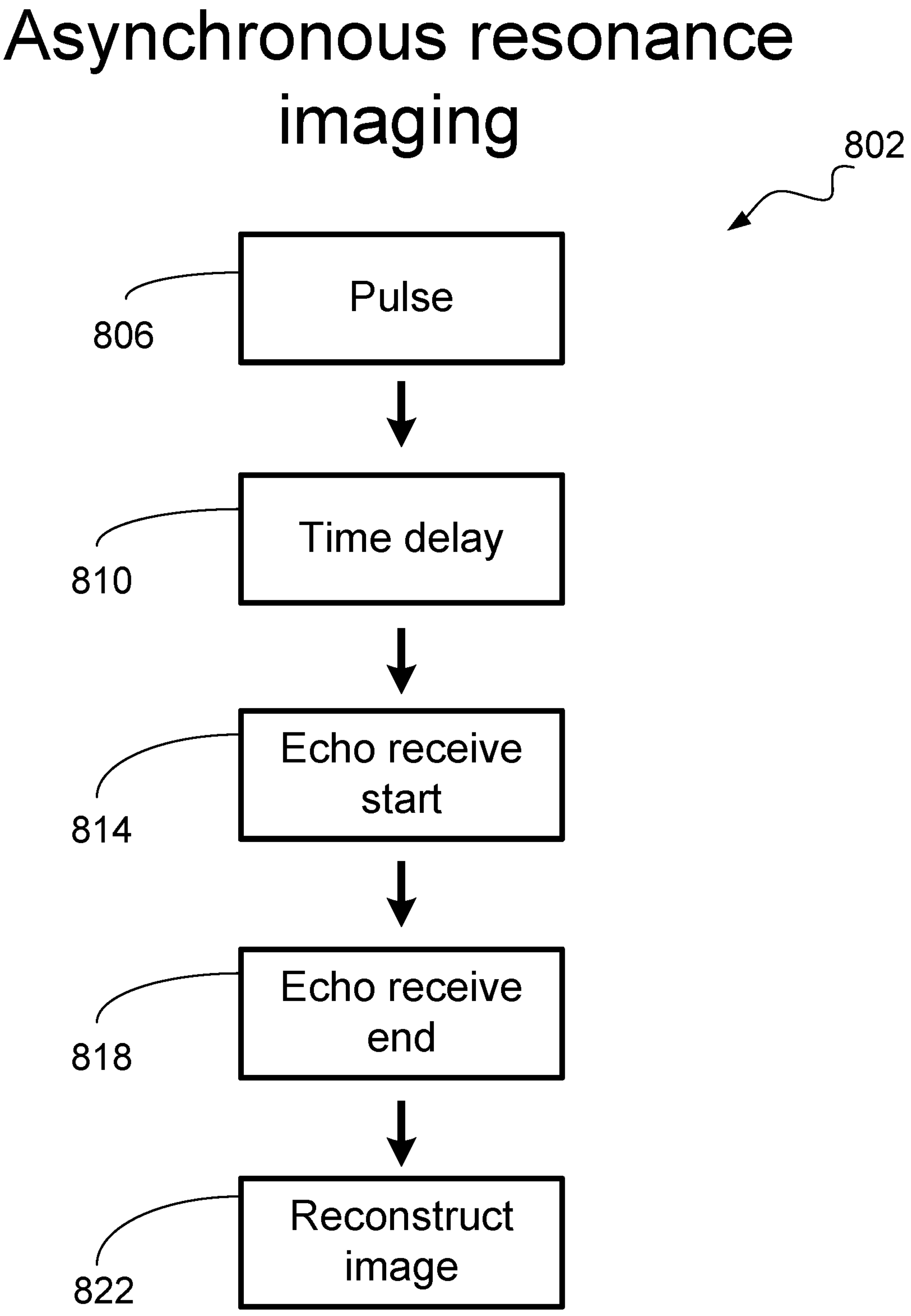
FIG. 8 illustrates a block diagram of an example asynchronous resonance imaging (ARI) technique.

FIG. 8 illustrates a block diagram of an example asynchronous resonance imaging (ARI) technique/sequence 802. At 806, at least one pulse may be generated into target tissue. At 810, a (e.g., predetermined and/or user adjustable) time delay may be observed before any receipt of one or more echo pulses/signals. At 814, receipt of one or more echo signals may begin. At 818, receipt of one or more echo signals may end. At 822, the received echo signals may be used to construct/reconstruct at least one image.

In one or more scenarios, perhaps while a typical ringdown artifact may originate at a feature in the image and propagate to the bottom of the image, among other scenarios, asynchronous resonance imaging may create a double ringdown artifact(s). In a double ringdown artifact, two ringdown artifacts may originate from the needle tip, one may propagate to the bottom of the image and the other may propagate to the top of the image. The narrowest point of the ringdown artifact(s) may be at the needle tip. They may increase in width as they propagate towards the top and/or bottom of the image, perhaps for example creating an "X" type of shape (e.g., the letter "X", an hourglass, etc.). The needle tip may be located at the narrowest point of the double ringdown artifact.

The term "double ringdown artifact" is a term of art corresponding to the technologies described herein. The term "ringdown artifact" is a technical term in the art which means a vertical line that may be composed of repeating horizontal lines, starting at the object in question (e.g., a needle tip). The ringdown artifact may propagate to the bottom of the image and/or may sometimes spread laterally with increasing depth. A double ringdown artifact may include at least two (2) ringdown artifacts originating from the needle tip. One of the ringdown artifacts may propagate to the bottom of the image/screen. Another ringdown artifact may propagate to the top of the image/screen. The upwards propagating ringdown artifact may be created by the one or more time delays as described herein.

Perhaps similar to a ringdown artifact in standard B-mode imaging, a double ringdown artifact may be composed of short, repeating horizontal lines, or may appear confluent, and might only be partially visualized. Bilateral "searchlight" lines, with a slope approximately parallel to the edges of the lower ringdown artifact, may sometime appear lateral to the double ringdown artifact. The double ringdown artifact is a concept covered by one or more technologies and/or techniques described herein.

Figure 9:
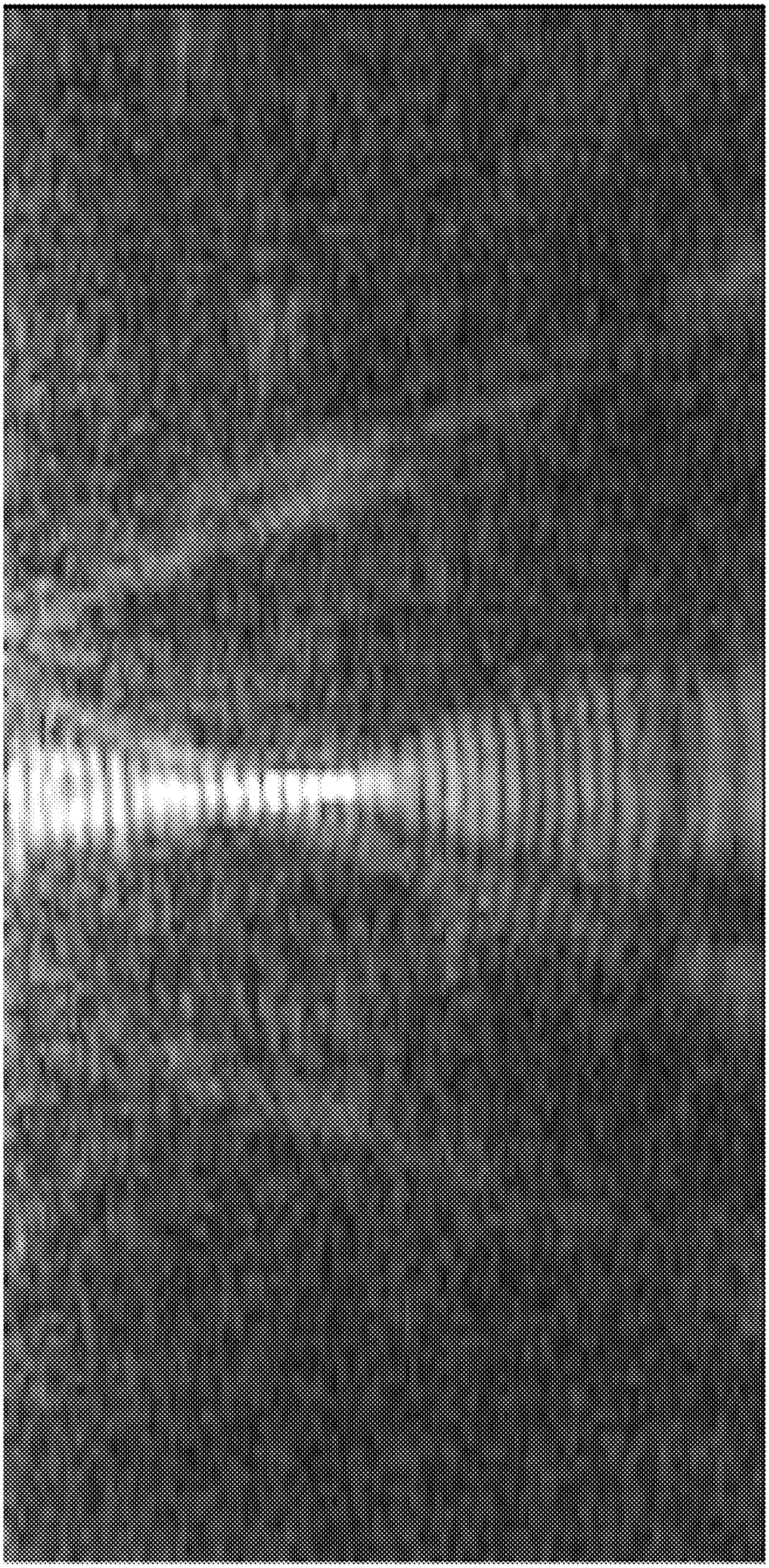
FIG. 9 illustrates an example of a double ringdown artifact composed of short, repeating horizontal lines.
Figure 10:
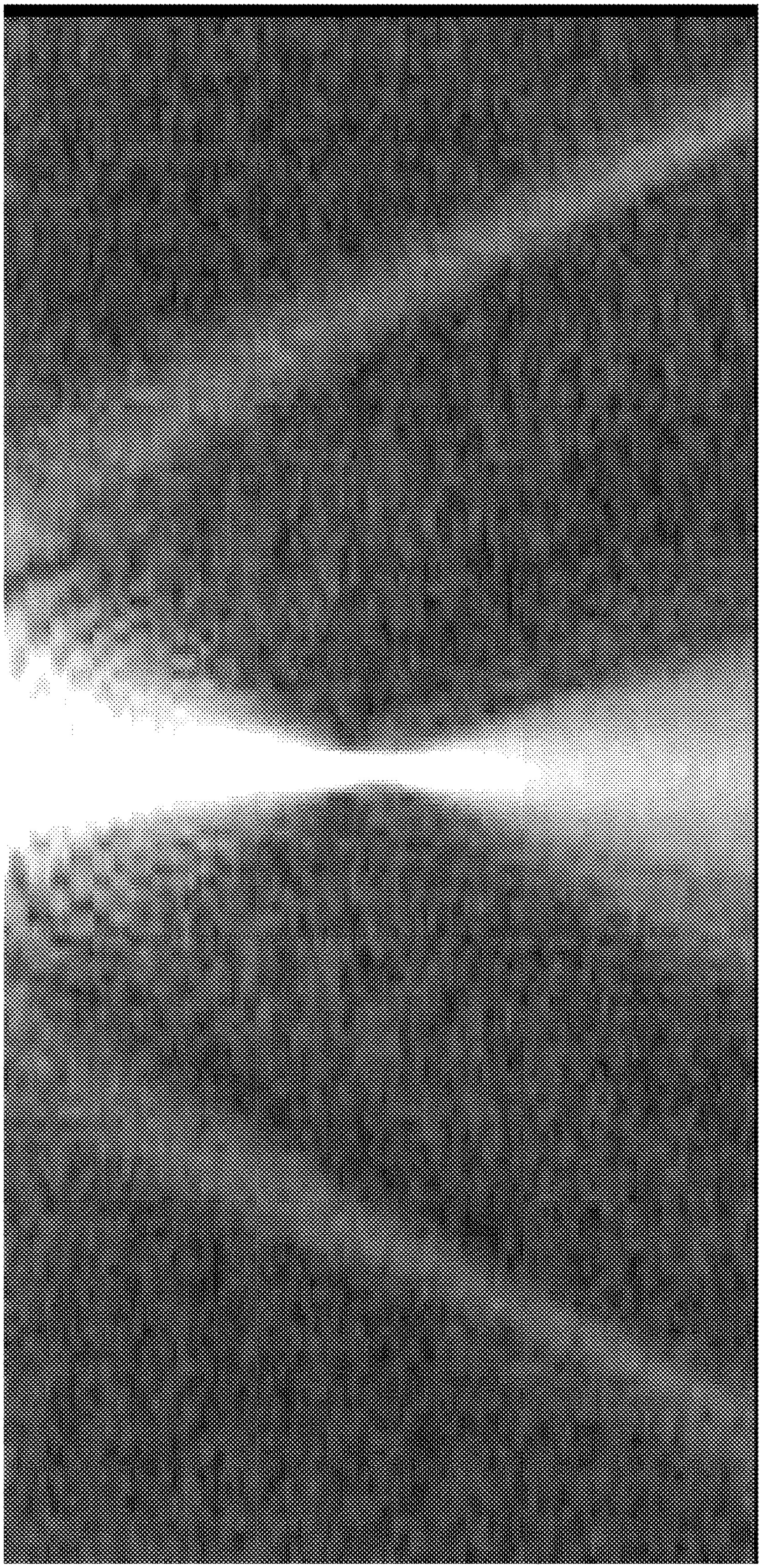
FIG. 10 illustrates an example of a double ringdown artifact with confluent appearance and bilateral "searchlight" lines.
Figure 11:
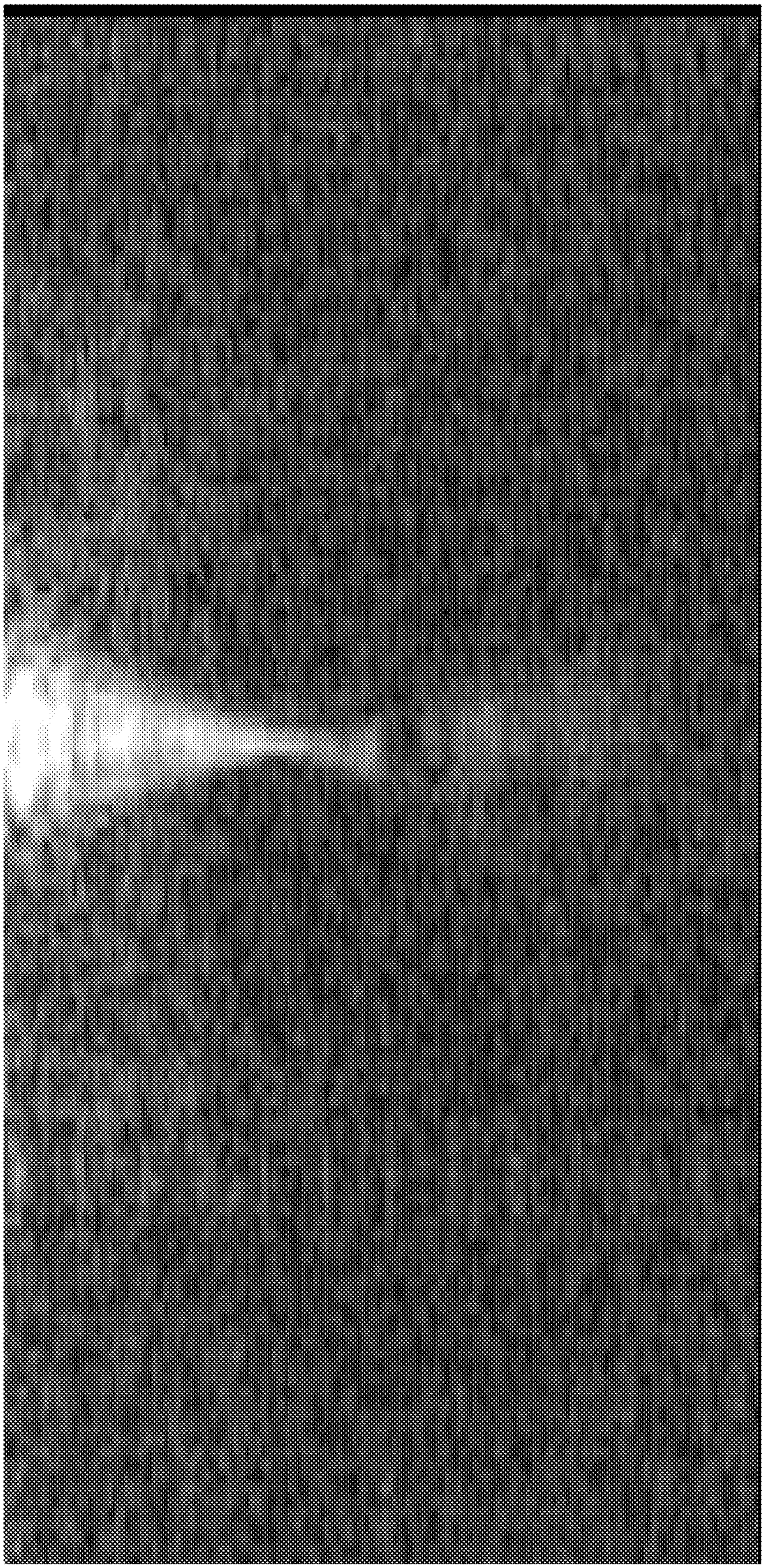
FIG. 11 illustrates an example of a double ringdown artifact with an incompletely visualized lower portion.

Examples of double ringdown artifacts created by asynchronous resonance imaging are illustrated in FIG. 9, FIG. 10, and FIG. 11. FIG. 9 illustrates an example of a double ringdown artifact composed of short, repeating horizontal lines. FIG. 10 illustrates an example of a double ringdown artifact with confluent appearance and bilateral "searchlight" lines. FIG. 11 illustrates an example of a double ringdown artifact with an incompletely visualized lower portion.

In one or more scenarios, the pulse echo principle might not apply to the double ringdown artifact in asynchronous resonance imaging. It may apply to soft tissue echoes. The location of the needle tip may be accurately identified by the narrowest point of the double ringdown artifact, irrespective of increasing and/or decreasing the time delay. For example, an asynchronous resonance image may be acquired with a time delay of 40 microseconds and a needle tip in the image plane at a true physical depth of 7 millimeters, that may produce an image with a double ringdown artifact with a narrowest point at 7 millimeters depth. Using the soft tissue speed of sound constant of 1.54 millimeters per microsecond, the pulse echo principle may predict that decreasing and/or increasing the time delay by 5 microseconds may increase or decrease, respectively, the depth of the narrowest point of the double ringdown artifact by 3 millimeters.

In one or more scenarios, in practice for example, images acquired with time delays of 35, 40, or 45 microseconds may (e.g., may all) result in a narrowest point of the double ringdown artifact at 7 millimeters depth, corresponding to the true physical depth of the needle tip. In contrast, any soft tissue features may be 6 millimeters deeper in the 35 microsecond time delay image as compared to the 45 microsecond time delay image. An example is illustrated in FIG. 12A, FIG. 12B, and FIG. 12C.

Figure 12A:
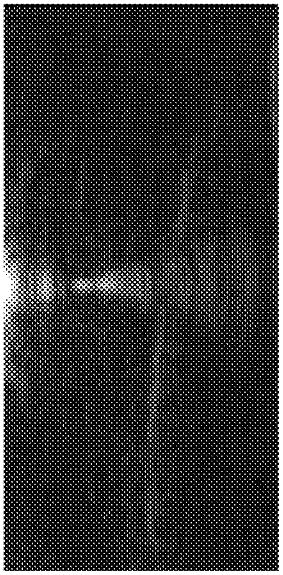
FIG. 12A illustrates an example needle tip image obtained with asynchronous resonance imaging with a 35 microsecond time delay.
Figure 12B:
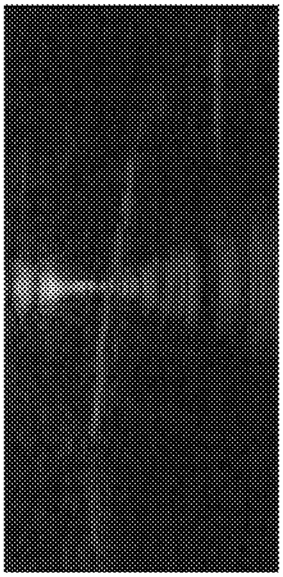
FIG. 12B illustrates an example needle tip image obtained with asynchronous resonance imaging with a 40 microsecond time delay.
Figure 12C:
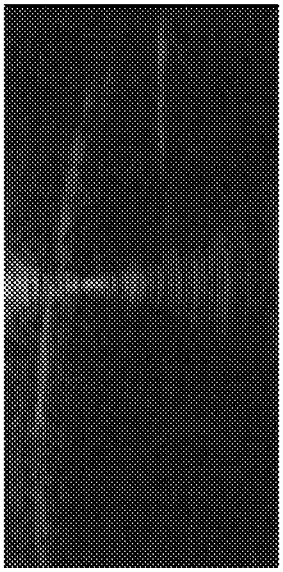
FIG. 12C illustrates an example needle tip image obtained with asynchronous resonance imaging with a 45 microsecond time delay.

FIG. 12A, FIG. 12B, and FIG. 12C illustrate example needle tip images obtained with asynchronous resonance imaging with varied time delays. In FIG. 12A, the time delay was 35 microseconds. In FIG. 12B, the time delay was 40 microseconds. In FIG. 12C the time delay was 45 microseconds. The narrowest point of the double ringdown artifact remains at the same depth in FIG. 12A, FIG. 12B, and FIG. 12C, while soft tissue echoes, appearing as horizontal lines, decrease in depth as the time delay is increased.

Focused and plane wave are at least two pulse types that can be used in asynchronous resonance imaging. The energy of a focused pulse may be concentrated at a given depth and lateral position, known as the focal zone. The energy of a plane wave pulse may be distributed evenly across the lateral dimension of the imaging plane. For a focused pulse with a needle tip in the image plane, the conspicuity of the double ringdown artifact may be greatest if the needle tip is at the focal zone, and/or may decrease with increasing distance from the needle tip to the focal zone. For a plane wave pulse, the conspicuity of the double ringdown artifact may be similar for any location of the needle tip within the image. If all other settings are identical, for example, a focused pulse with a needle tip within the focal zone may produce a more conspicuous double ringdown artifact than a plane wave pulse. Examples of the effect of needle tip position on double ringdown artifact conspicuity using focused and plane wave pulses are illustrated in FIG. 13, FIG. 14, FIG. 15, and FIG. 16.

Figure 13:
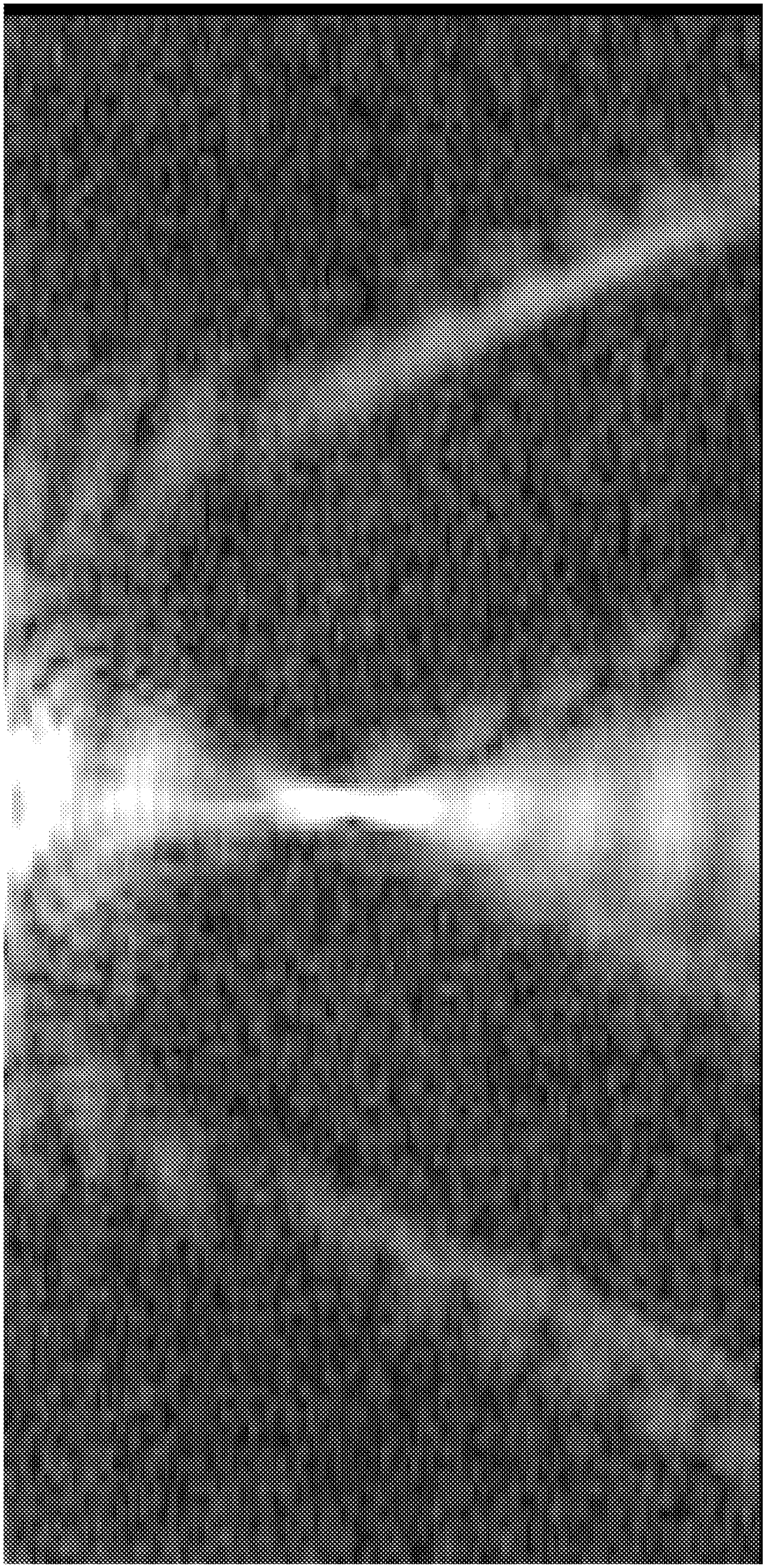
FIG. 13 illustrates an example of a focused pulse, focal zone and needle tip position in a center of an image.
Figure 14:
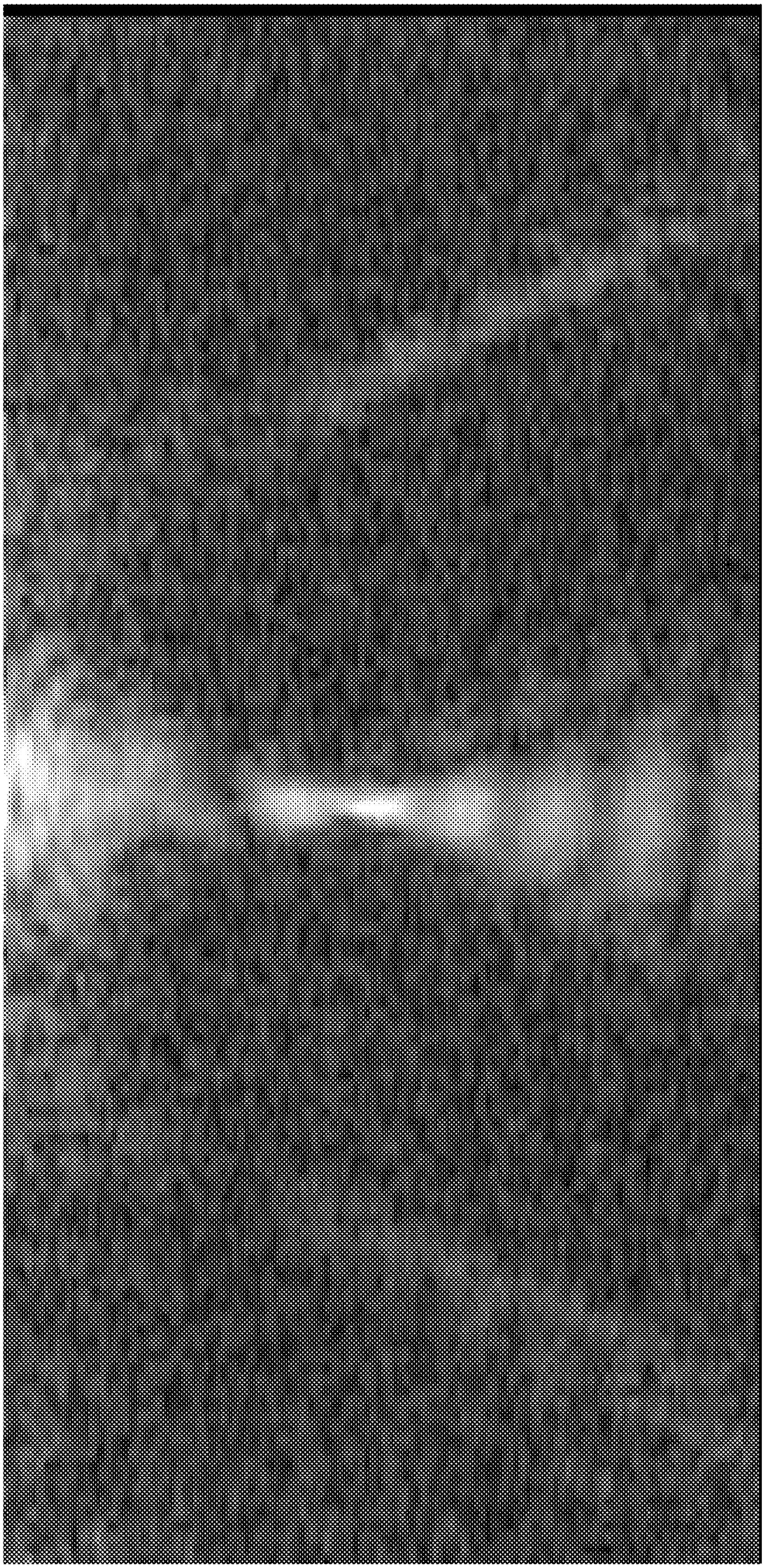
FIG. 14 illustrates an example of a plane wave pulse, needle tip position in a center of an image.
Figure 15:
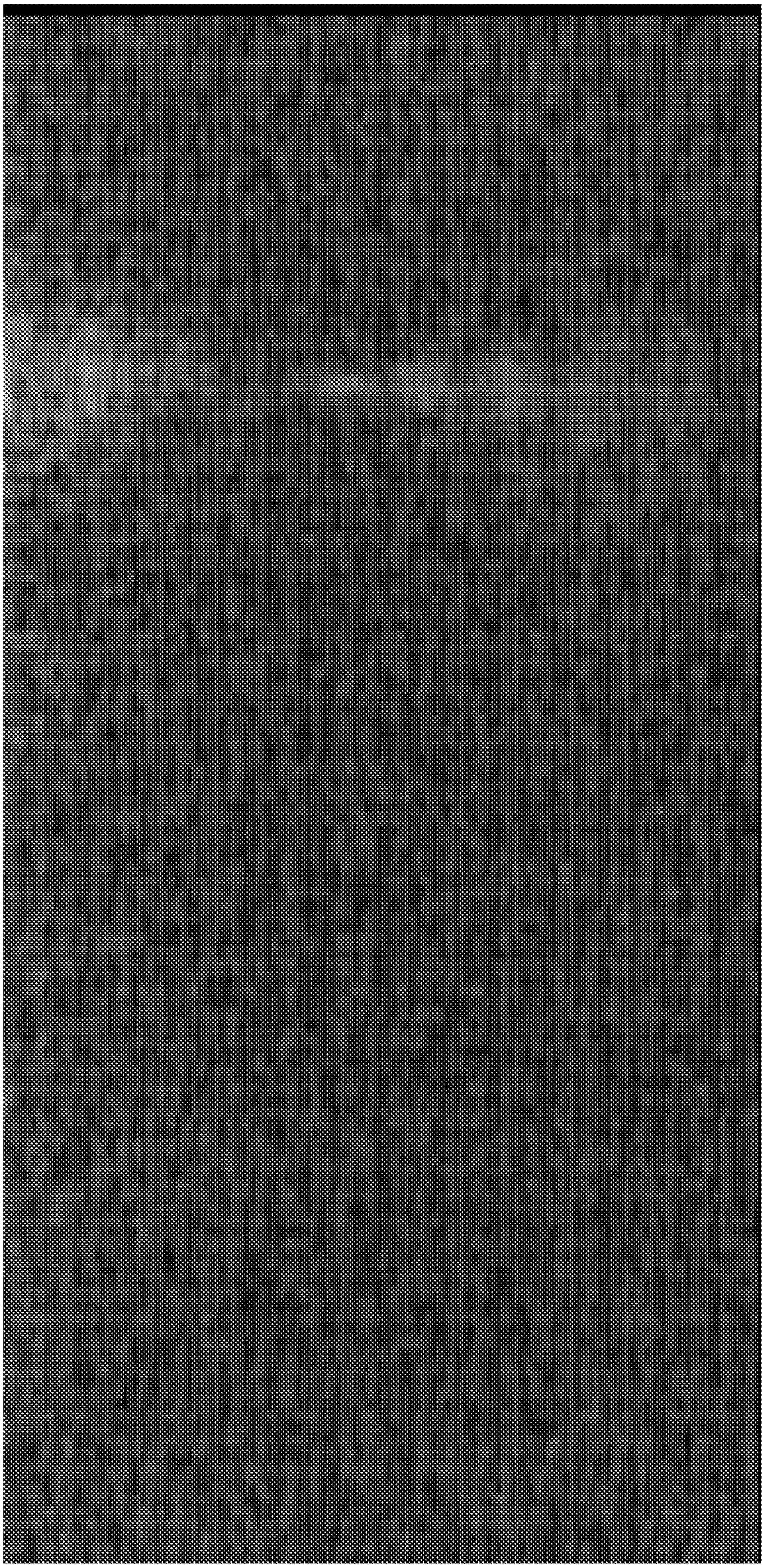
FIG. 15 illustrates an example of a focused pulse, focal zone in a center of an image, in which the needle tip position is on a right side of the image.
Figure 16:
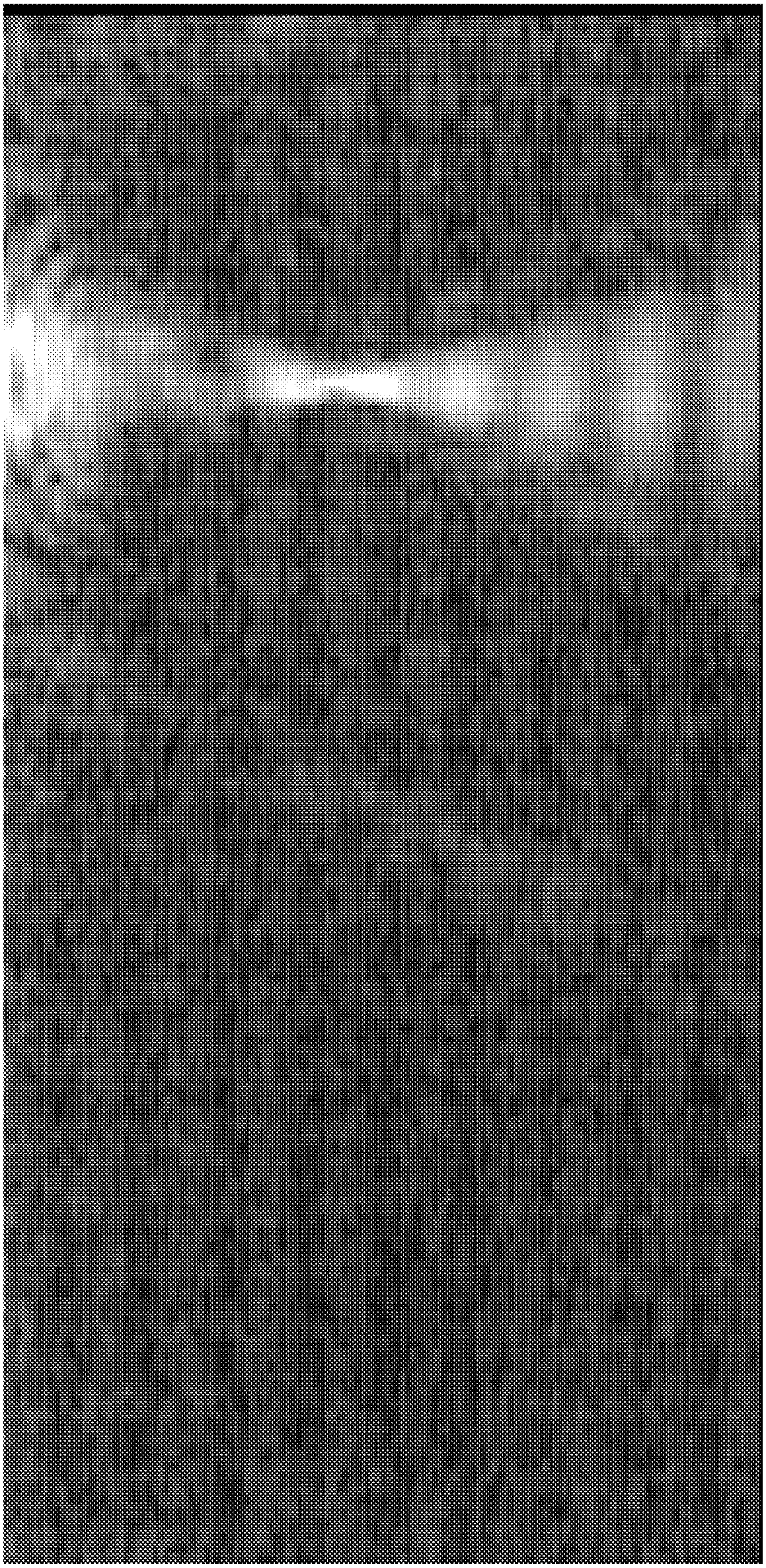
FIG. 16 illustrates an example of a plane wave pulse, in which the needle tip position is on a right side of the image.

FIG. 13 illustrates an example of a focused pulse, focal zone and needle tip position in a center of an image. FIG. 14 illustrates an example of a plane wave pulse, needle tip position in a center of an image. FIG. 15 illustrates an example of a focused pulse, focal zone in a center of an image, in which the needle tip position is on a right side of the image. FIG. 16 illustrates an example of a plane wave pulse, in which the needle tip position is on a right side of the image. The highest conspicuity double ringdown artifact may be in the focused pulse image with the focal zone and the needle tip position coinciding. The lowest conspicuity double ringdown artifact may be in the focused pulse image with the focal zone and the needle tip position separated. The double ringdown artifact is well visualized in both plane wave images, and/or may be less conspicuous than the double ringdown artifact in the focused pulse image with the focal zone and the needle tip position coinciding.

In one or more scenarios, there may be a plurality of double ringdown artifacts. The double ringdown artifact(s) that may be indicative of the location of the needle tip may be the one that is "conspicuous" and/or is the last double ringdown artifact that may be seen as the probe is moved away from the needle. The term "conspicuity" is a term radiologists may use to indicate how much a given feature may stand out from the surrounding structures on the image. Conspicuity may be a ratio of the average grayscale intensity of the structure of interest to the average grayscale intensity of the surrounding pixels, for example.

A conspicuous double ringdown artifact may (e.g., may only) be produced perhaps for example if the needle tip is within the imaging plane. Weak double ringdown artifacts may be produced by other positions on the needle. Such artifacts can be distinguished from the conspicuous ringdown artifact(s) at the needle tip by moving the imaging probe. Conspicuous double ringdown artifacts may be produced by other positions on the needle. These positions may be sufficiently distant from the needle tip such that they can be distinguished from the needle tip double ringdown artifact by moving the imaging probe, for example.

To detect a needle tip location using focused pulses, among other scenarios, one or more, or many, focused pulse asynchronous resonance imaging acquisitions with varied focal zones may (e.g., must) be performed, so that images are acquired with focal zones close to all possible locations of the needle tip in the image. The images are then processed, with the image with the most conspicuous double ringdown artifact retained, perhaps with one or more, or all, other images discarded, for example. In one or more scenarios, a single plane wave pulse asynchronous resonance imaging acquisition may be sufficient to generate a double ringdown artifact for any location of the needle tip within the image.

Figure 17:
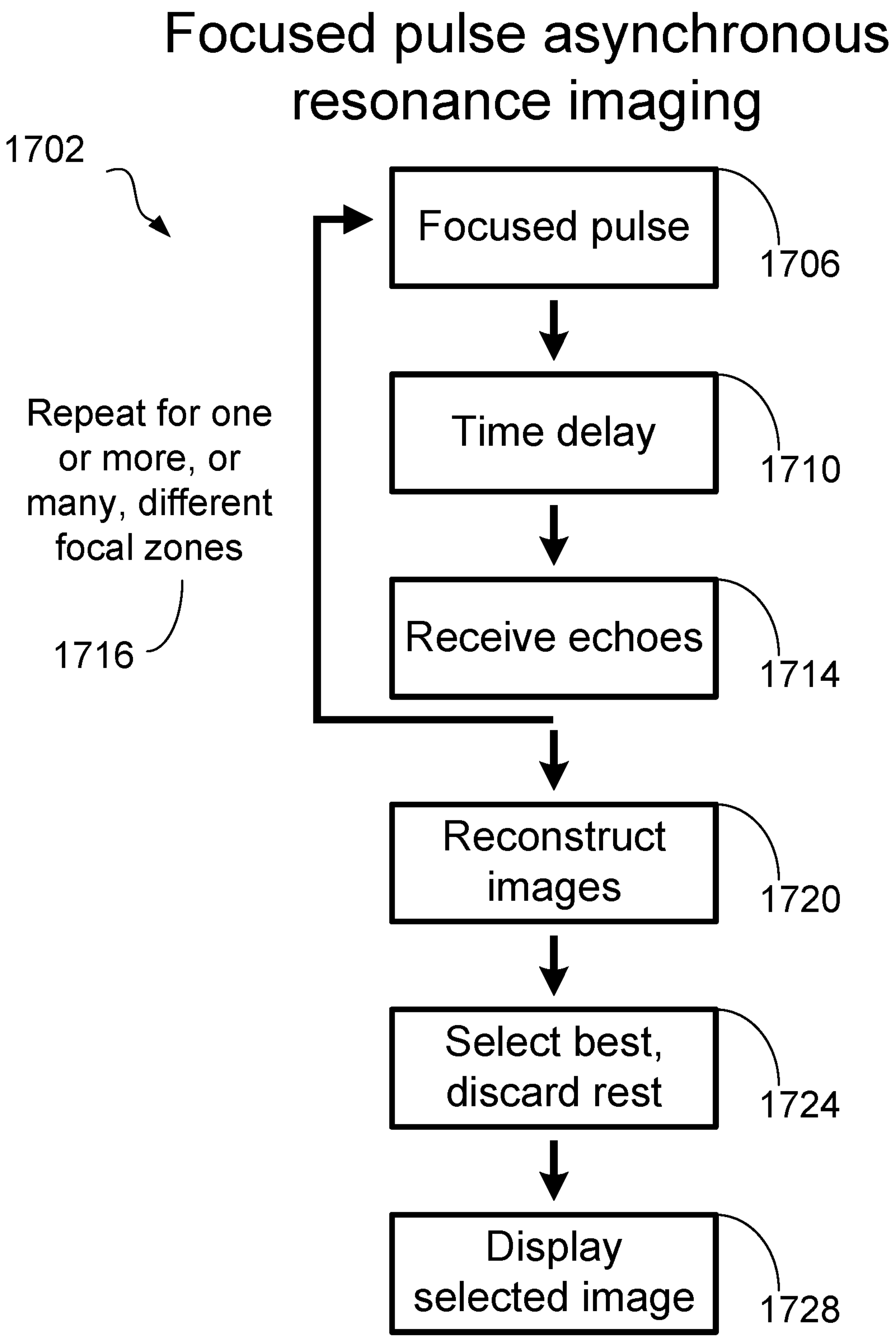
FIG. 17 illustrates a block diagram describing the imaging sequence for a focused wave pulse asynchronous resonance imaging.

FIG. 17 illustrates a block diagram describing the imaging sequence/technique 1702 for a focused wave pulse asynchronous resonance imaging. At 1706, at least one focused wave pulse may be generated/transmitted into target tissue. At 1710, a (e.g., predetermined and/or user adjustable) time delay may be observed before any echo signals/pulses may be received. At 1714, receipt of one or more echo pulses/signals may begin. At 1716, one or more of the elements 1706, 1710, and/or 1714 can be repeated one or more times. At 1720, one or more images may be reconstructed based on the received one or more echo signals/pulses. At 1724, one or more images may be selected (e.g., as better/best images) and/or one or more images may be discarded as less than useful, for example. At 1728, one or more images (e.g., compound and other images) may be displayed.

Figure 18:
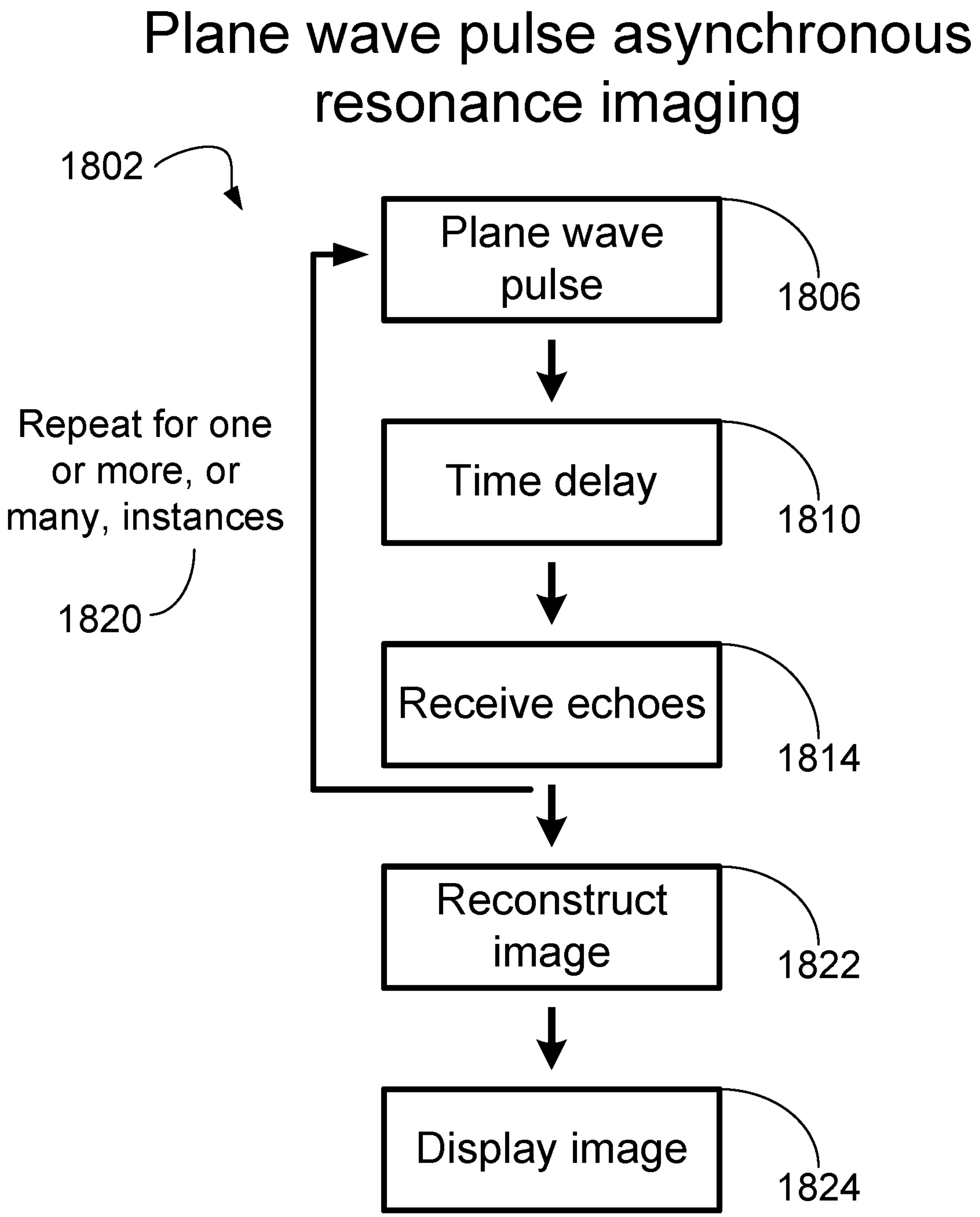
FIG. 18 illustrates a block diagram describing the imaging sequence for a plane wave pulse asynchronous resonance imaging.

FIG. 18 illustrates a block diagram describing the imaging sequence/technique 1802 for a plane wave pulse asynchronous resonance imaging. At 1806, at least one plane wave pulse may be generated/transmitted into target tissue. At 1810, a (e.g., predetermined and/or user adjustable) time delay may be observed before any echo signals/pulses may be received. At 1814, receipt of one or more echo pulses/signals may begin. At 1820, one or more of the elements 1806, 1810, and/or 1814 can be repeated one or more times. At 1822, one or more images may be reconstructed based on the received one or more echo signals/pulses. At 1824, one or more images (e.g., compound and other images) may be displayed.

Perhaps due to the large number of image acquisitions that may be useful (e.g., required) to create a single image frame with focused pulse asynchronous resonance imaging, among other scenarios, a much higher frame rate can be achieved with plane wave pulse asynchronous resonance imaging. The higher frame rate of plane wave pulse asynchronous resonance imaging may enable use of a greater number of image acquisitions for radiofrequency accumulation and average imaging to create a (e.g., single) image frame.

The frame rate of focused pulse asynchronous resonance imaging can be increased by combining one or more, or multiple, pulses with a (e.g., single) echo receive period. In one or more scenarios, the pulse repetition frequency may be limited by hardware typical of medical imaging ultrasound machines, and/or patient safety bioeffects concerns. The number of pulses combined with a (e.g., single) echo receive period may be limited by the time duration between the first and last pulse, as the echoes from the first pulse may become weaker as this duration increases.

For a pulse of a given duration, the bioeffects may be greater for a focused pulse than a plane wave pulse, perhaps for example due to the concentration of the energy of a focused pulse on the focal zone. Therefore, longer pulse durations can be achieved using a plane wave pulse without limitations from subject/patient safety bioeffects concerns. As bandwidth is inversely proportional to pulse duration, a longer pulse duration may achieve a narrower bandwidth, perhaps allowing the ultrasound pulse energy to be more closely distributed around the needle's resonant frequency, for example.

In one or more scenarios, the needle tip double ringdown artifact echoes in asynchronous resonance imaging may be weak. The weakness may be due to the low intensity of needle tip ringdown artifact echoes relative to surrounding soft tissue, and/or the weakening of one or more, or all, echoes during the time delay. It may be useful (e.g., helpful, necessary, etc.) to use a higher level of gain in asynchronous resonance imaging perhaps for example as compared to standard B-mode imaging. The time gain compensation (TGC) may be increased to maximum at one or more, or all, levels of the image. In one or more scenarios, a processing gain multiplication factor of 15 may be applied to the pixel intensity data, perhaps for example before compression, among other phases of the sequence.

Figure 19:
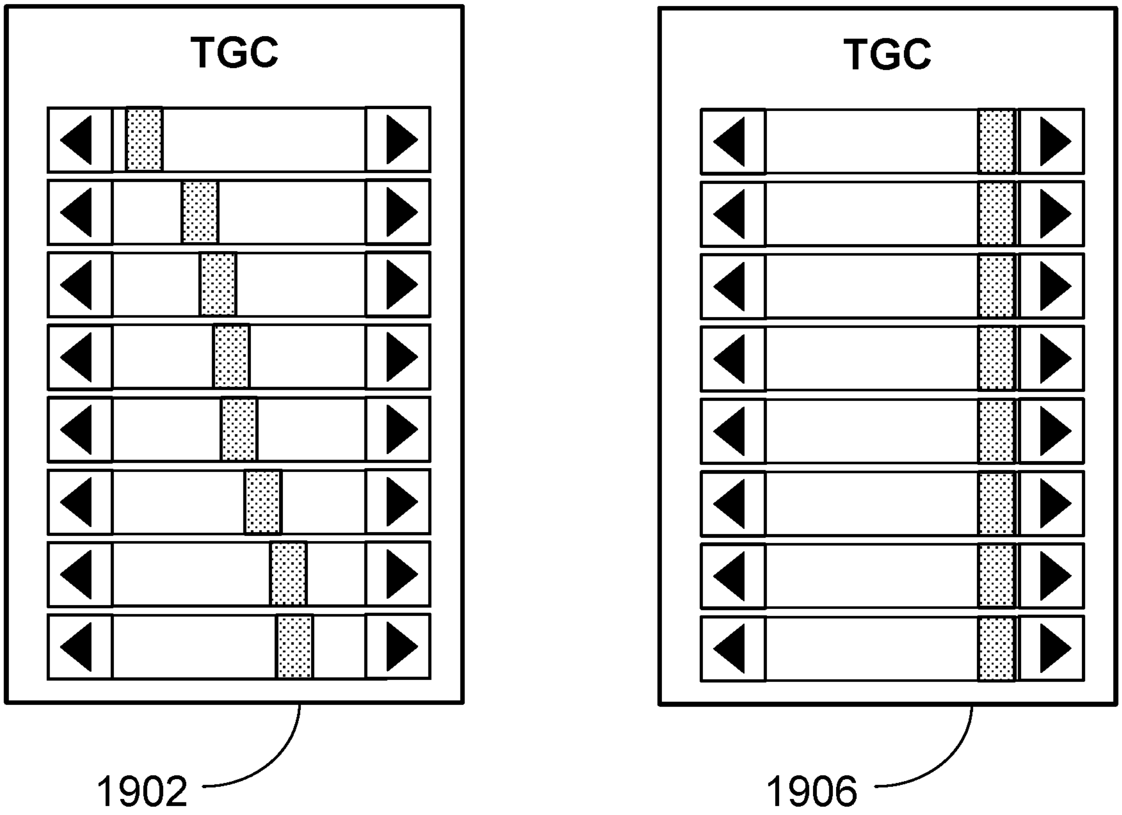
FIG. 19 illustrates examples of TGC at typical levels for standard B-mode imaging and at maximum image levels as used in asynchronous resonance imaging.

FIG. 19 illustrates examples of TGC at (e.g., typical) levels for standard B-mode imaging and at maximum at one or more, or all, image levels as used in asynchronous resonance imaging, for example. At 1902, TGC at typical levels for standard B-mode imaging are illustrated. At 1906, TGC at maximum at one or more, or all, image levels as used in asynchronous resonance imaging are illustrated.

Figure 20:
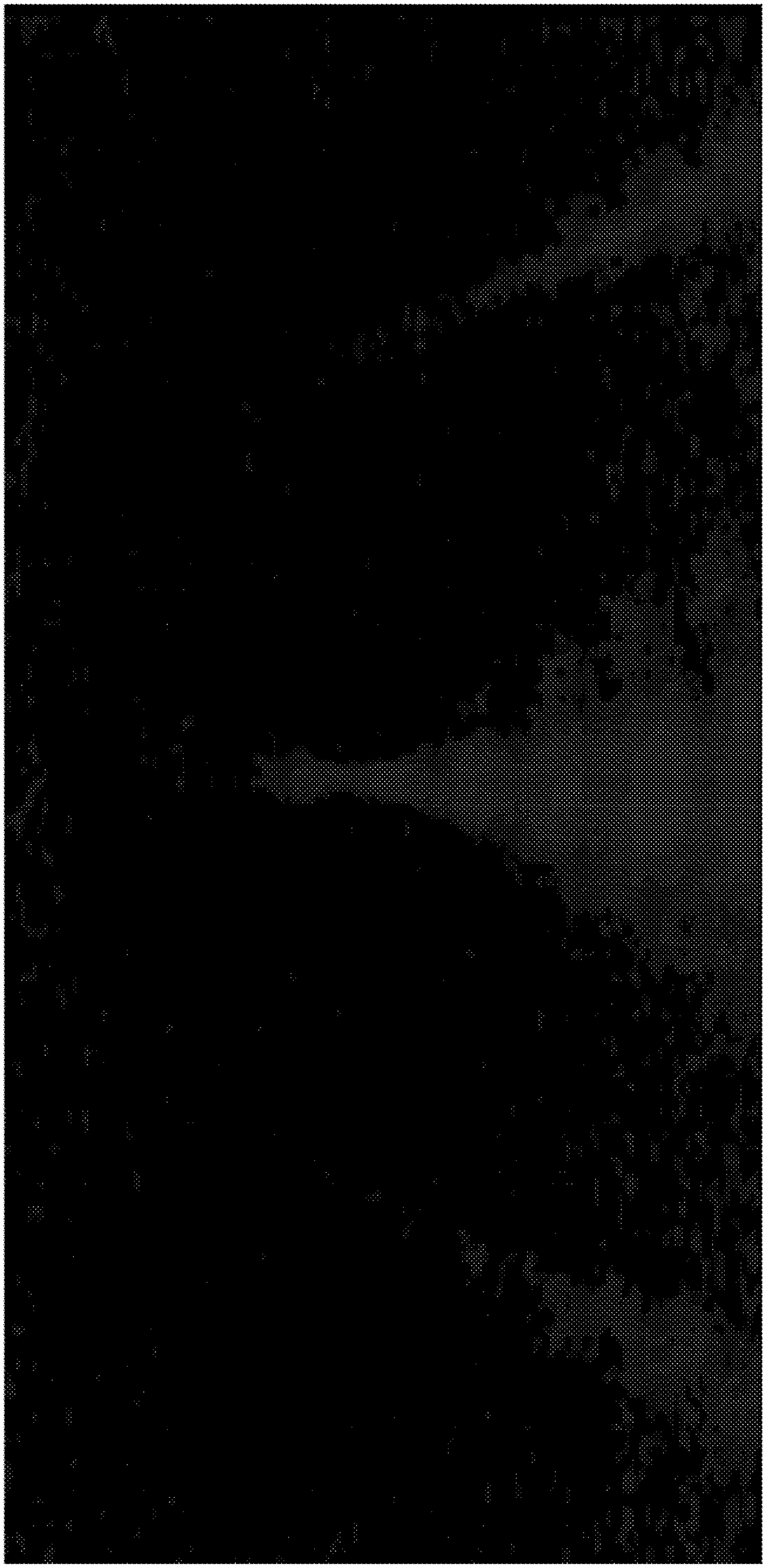
FIG. 20 illustrates an example double ringdown artifact visualization with TGC at typical B-mode levels and processing gain multiplier of 1.
Figure 21:
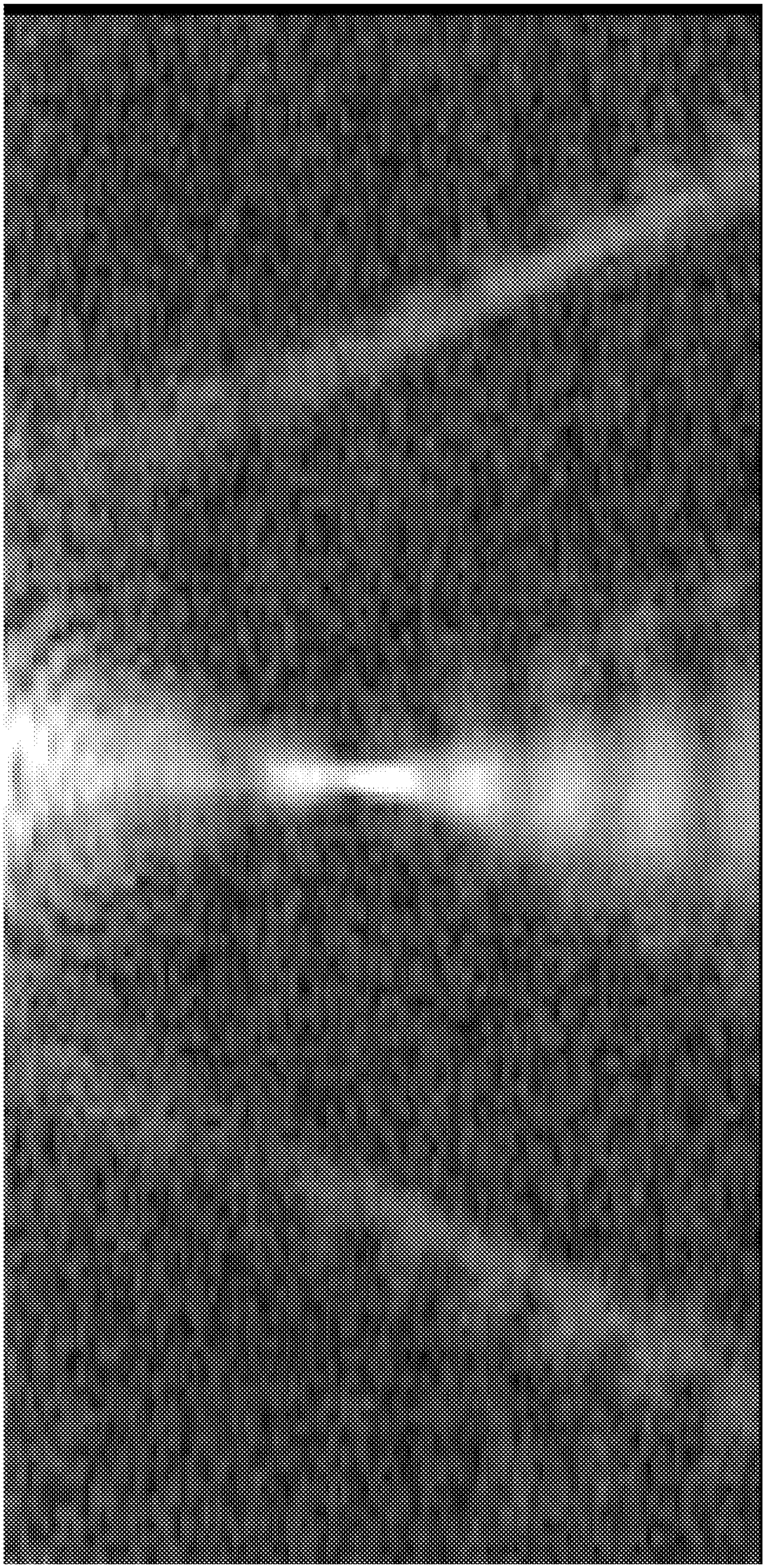
FIG. 21 illustrates an example double ringdown artifact visualization with TGC at maximum at all levels and a processing gain multiplier of 15.

FIG. 20 and FIG. 21 illustrate examples of needle tip asynchronous resonance images obtained with typical B-mode gain settings. Typical TGC levels and a processing gain multiplier of 1 may be used, which may result in poor visualization of the double ringdown artifact. More appropriate asynchronous resonance imaging gain settings of TGC at maximum at one or more, or all, levels and processing gain multiplier of 15, which may result in more conspicuous appearance of the double ringdown artifact.

In FIG. 20 and FIG. 21, illustrated examples of needle tip asynchronous resonance images obtained with varied gain settings. In FIG. 20, with typical B-mode gain settings, with TGC at typical B-mode levels and processing gain multiplier of 1, a double ringdown artifact may be poorly visualized. In FIG. 21, with appropriate asynchronous resonance imaging gain settings, with TGC at maximum at one or more, or all, levels and a processing gain multiplier of 15, a double ringdown artifact may be (e.g., well) visualized.

Perhaps in order to distinguish weak double ringdown artifact echoes from surrounding noise and thereby increase the conspicuity of the double ringdown artifact, among other reasons, it may be helpful to accumulate and/or average radiofrequency data from one or more, or multiple, image acquisitions.

To perform radiofrequency data accumulation and averaging, when echo radiofrequency data is acquired, it is not reconstructed to pixel intensity data. Instead, another image acquisition may be performed, and the newly acquired and previously acquired radiofrequency data may be summed. This process may be repeated for a (e.g., predetermined) number of image acquisitions, perhaps for example after which the summed radiofrequency data may be averaged. The averaged radiofrequency data may be used to reconstruct pixel intensity data, and a (e.g., single) image frame may be displayed.

Figure 22:
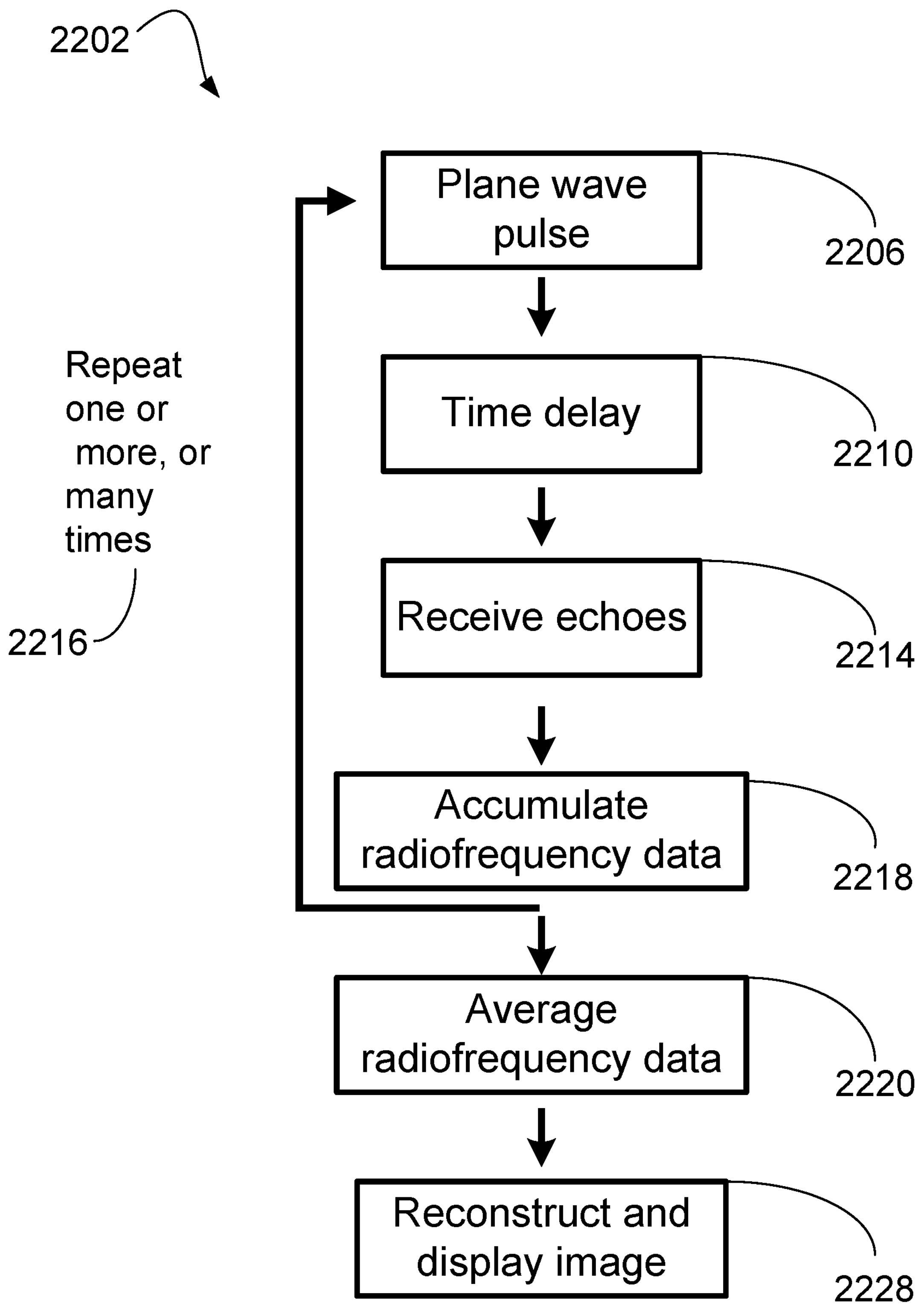
FIG. 22 illustrates a block diagram of an example asynchronous resonance imaging radiofrequency data accumulation and averaging sequence.

FIG. 22 illustrates a block diagram of an example asynchronous resonance imaging radiofrequency data accumulation and averaging sequence/technique 2202. In FIG. 22, radiofrequency data from, for example, 10 image acquisitions are accumulated and averaged to create a (e.g., single) displayed image frame. At 2206, at least one plane wave pulse may be generated/transmitted into target tissue. At 2210, a (e.g., predetermined and/or user adjustable) time delay may be observed before any echo signals/pulses may be received. At 2214, receipt of one or more echo pulses/signals may begin. At 2216, one or more of the elements 2206, 2210, and/or 2214 can be repeated one or more times. At 2218, radiofrequency data may be accumulated. At 2220, the radiofrequency data may be averaged. At 2228, one or more images (e.g., compound and other images) may be reconstructed and/or displayed.

Figure 23:
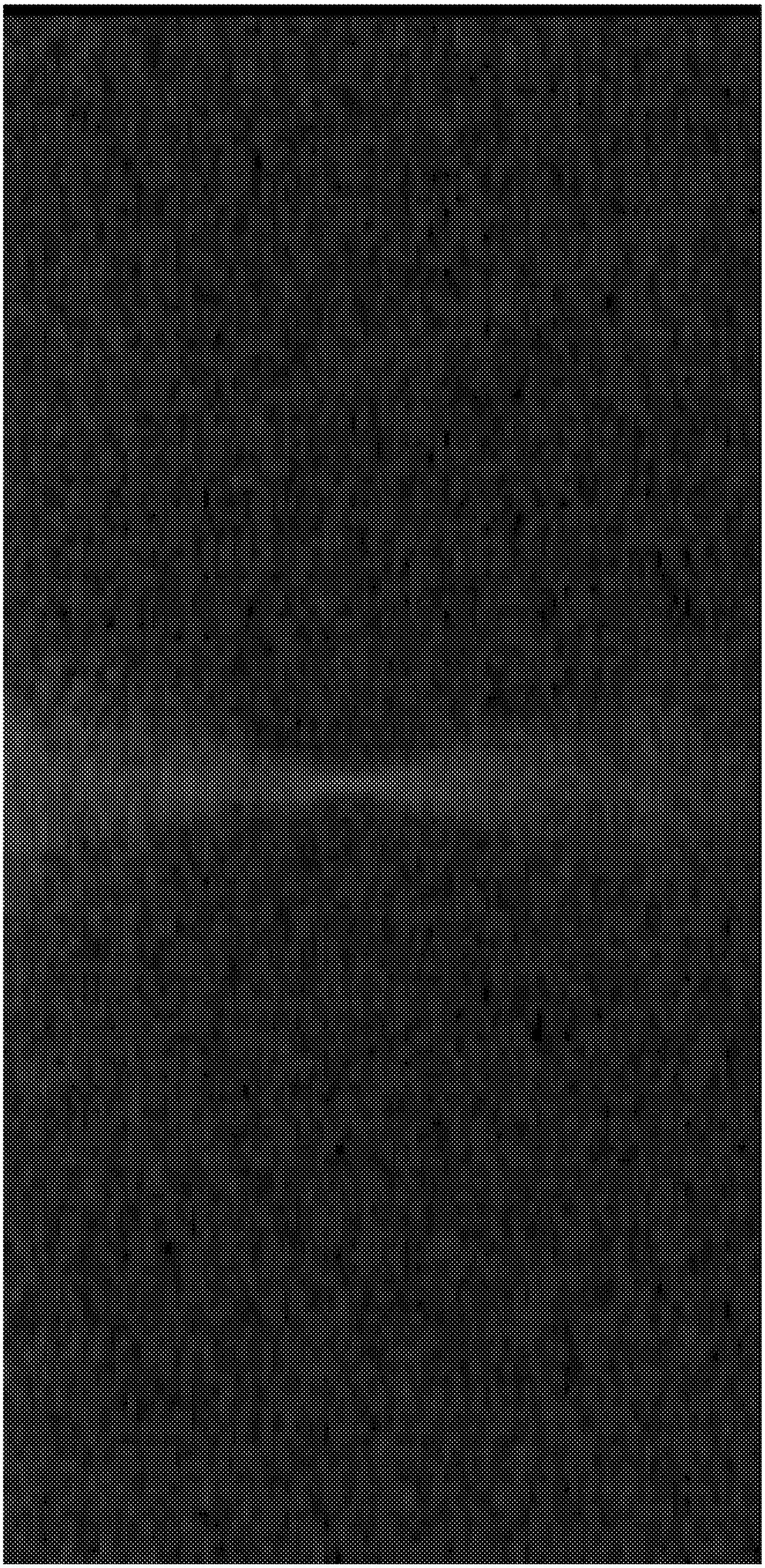
FIG. 23 illustrates an example single image acquisition with no radiofrequency data accumulation and averaging where a needle tip double ringdown artifact may be poorly visualized.
Figure 24:
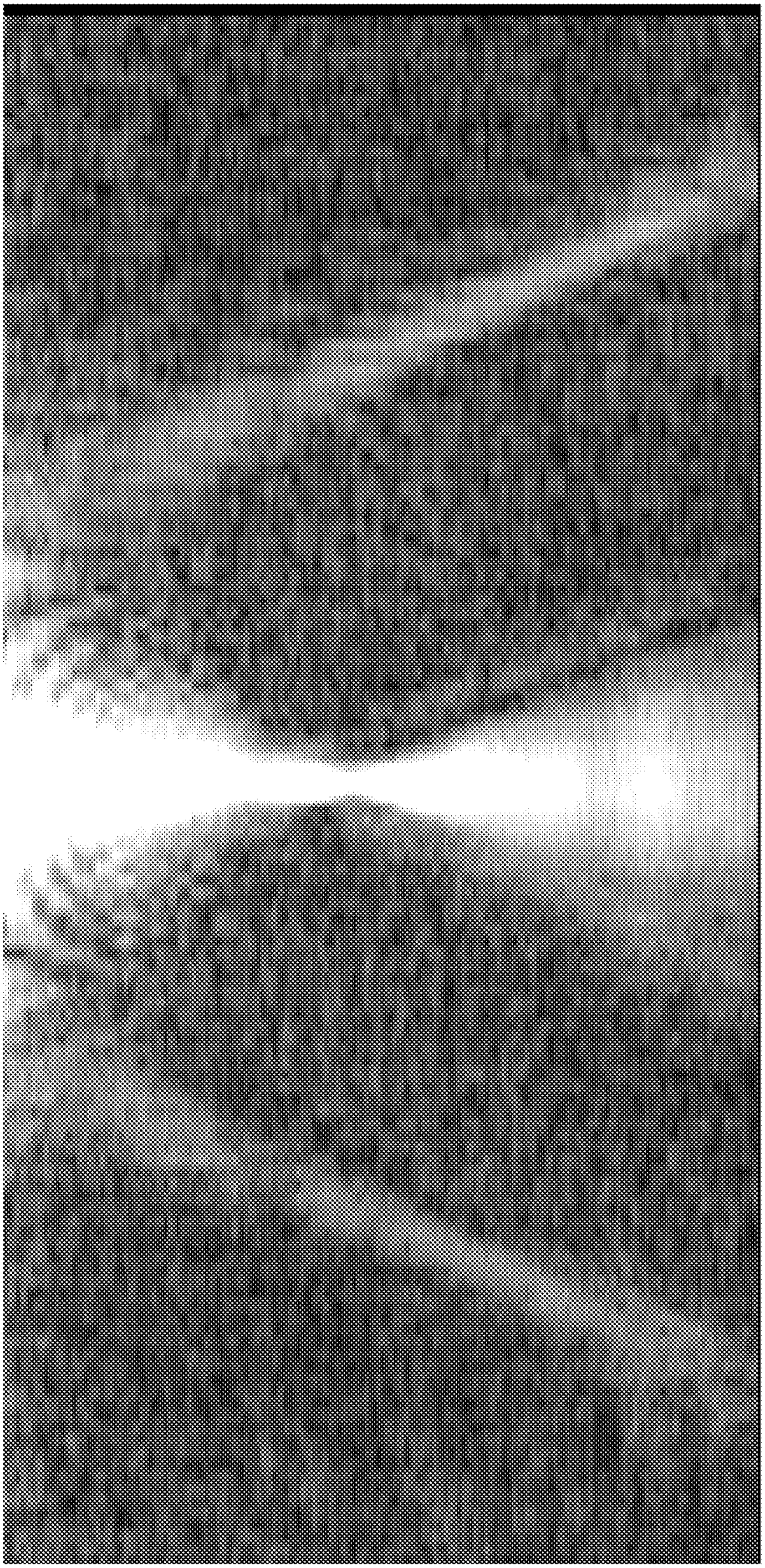
FIG. 24 illustrates an example radiofrequency data accumulation and averaging from multiple image acquisitions to create a single image frame where a needle tip double ringdown artifact may be well visualized.

FIG. 23 and FIG. 24 respectively illustrate examples of asynchronous resonance images acquired with and without radiofrequency data accumulation and averaging. FIG. 23 illustrates an example single image acquisition, with no radiofrequency data accumulation and averaging, where a needle tip double ringdown artifact may be poorly visualized. FIG. 24 illustrates an example radiofrequency data accumulation and averaging from ten (10) image acquisitions, for example, to create a single image frame, where a needle tip double ringdown artifact may be well visualized.

Perhaps due to the higher frame rate of plane wave pulse asynchronous resonance imaging, among other scenarios, a higher number of image acquisitions can be used for radiofrequency data accumulation and averaging using plane wave pulses than using focused pulses.

In one or more scenarios, one or more, or multiple first pulse acquisition events may be performed perhaps before proceeding to the second pulse B-mode image acquisition. The radiofrequency data from these first pulse acquisition events may be accumulated and/or averaged to create a (e.g., single) first pulse image with increased conspicuity of the needle tip double ringdown artifact. For plane wave first pulse image acquisitions, some or all radiofrequency data from one or more, or each, acquisition event may be included in the averaging process. For focused pulse image acquisitions, radiofrequency data may be (e.g., may only be) averaged from acquisition events that include the same first pulse focal zones, for example.

Focused pulse(s) may require one or more, or multiple, rounds of acquiring ARI, and the following image processing to see which of the image(s) may contain the best example of a double ringdown artifact. Such a best example image may be used to combine with the B-mode image(s). The multiple rounds might not be necessary for plane wave technologies, where for example one pulse may serve the whole screen/image.

In one or more scenarios, for example in which there are first transmitted pulse signals and second transmitted pulse signals, the first pulse signals may be focused pulses. An acquisition event may be composed of one or more focused pulses, with varied focal zones, that may be combined with a (e.g., single) echo receive period. Data from one or more, or multiple, acquisition events with different focal zones may be combined to create an image. A significant portion of the image may be composed of pixels in close proximity to a focal zone. The closer that the needle tip is to a focal zone, the more conspicuous the double ringdown artifact may be.

At least one benefit/advantage of using focused pulses is that more energy may be delivered to the needle tip and/or less energy may be delivered to the surrounding soft tissue. This may result in stronger needle tip echoes and/or weaker soft tissue echoes. This may result in increased conspicuity of the needle tip double ringdown artifact(s).

In one or more scenarios, a disadvantage of using focused first pulses may be that one or more, or multiple, acquisition events may be useful (e.g., required) to obtain the needle tip data for an entire image, perhaps as compared to a single acquisition event for a plane wave pulse. This may result in a lower frame rate which may involve less time being available for first pulse radiofrequency data accumulation and/or averaging and/or for second pulse B-mode imaging. Increased image processing may be required to combine the data from these one or more, or multiple, acquisition events into a needle tip image, further decreasing the frame rate.

In one or more scenarios, a low frame rate can be somewhat mitigated by using one or more, or multiple, focused pulses per acquisition event. The number of focused pulses per acquisition may be limited to a low number such as 5, for example. A higher/high number of pulses per acquisition event could result in decreased needle tip double ringdown artifact conspicuity at focal zones from earlier pulses, perhaps for example due to a longer effective delay period. One or more, or multiple, focused pulses in a given acquisition event could be separated by a short time, such as for example 10 microseconds from one focused pulse to the next. One or more factors such as pulse number, transmit voltage, and/or pulse duration could be limited by hardware factors such as the power supply of a typical medical ultrasound machine, among other factors.

In one or more scenarios, a disadvantage of using a focused first pulse may be that the duration of the first pulse may be limited by bioeffects on subject/patient soft tissue. This is because a focused pulse concentrates the ultrasound energy on a small area. This may result in increased maximum energy and/or power per area compared to an image obtained with a plane wave first pulse, for example.

In one or more scenarios, for example in which there are first transmitted pulse signals and second transmitted pulse signals, the first pulse signals may be plane wave pulses. As a plane wave pulse distributes the energy of the ultrasound pulse evenly across the lateral dimension of the image, a needle tip at a given depth may create a similarly conspicuous double ringdown artifact at one or more, or any, lateral position of the needle tip. An acquisition event may be composed of one or more plane wave pulses that may be combined with a (e.g., single) echo receive period. A (e.g., single) plane wave acquisition event may provide needle tip data for an entire image. This may produce a double ringdown artifact if the needle tip is located anywhere within the image.

At least one advantage of using a plane wave pulse is that needle tip data for an entire image may be obtained with a (e.g., single) acquisition event using a single first pulse, which may result in relatively high frame rates. Such high frame rates may provide increased time for first pulse radiofrequency data accumulation and/or averaging acquisition events. This may provide improved needle tip double ringdown artifact conspicuity. For second pulse B-mode image acquisition, improved soft tissue image quality may result.

As the energy of a plane wave first pulse is spread evenly across the lateral dimension of the beam aperture, the maximum energy per unit area may be less for a plane wave pulse than for a focused pulse. For a given pulse duration, the bioeffects on the subject/patient may be less for a plane wave pulse than for a focused pulse. This may allow for longer pulse durations for a plane wave pulse, for example.

In one or more scenarios, the conspicuity of the needle tip double ringdown artifact may be affected by a duration of the time delay between the ultrasound transmit pulse and the start of the echo receive period. A time delay that may be relatively too short may result in the presence of one or more tissue echoes which may obscure the double ringdown artifact. A time delay that may be relatively too long may result in (e.g., excessive) weakening of the double ringdown artifact echoes. This may cause the double ringdown artifact to be poorly visualized or absent.

Figure 25:
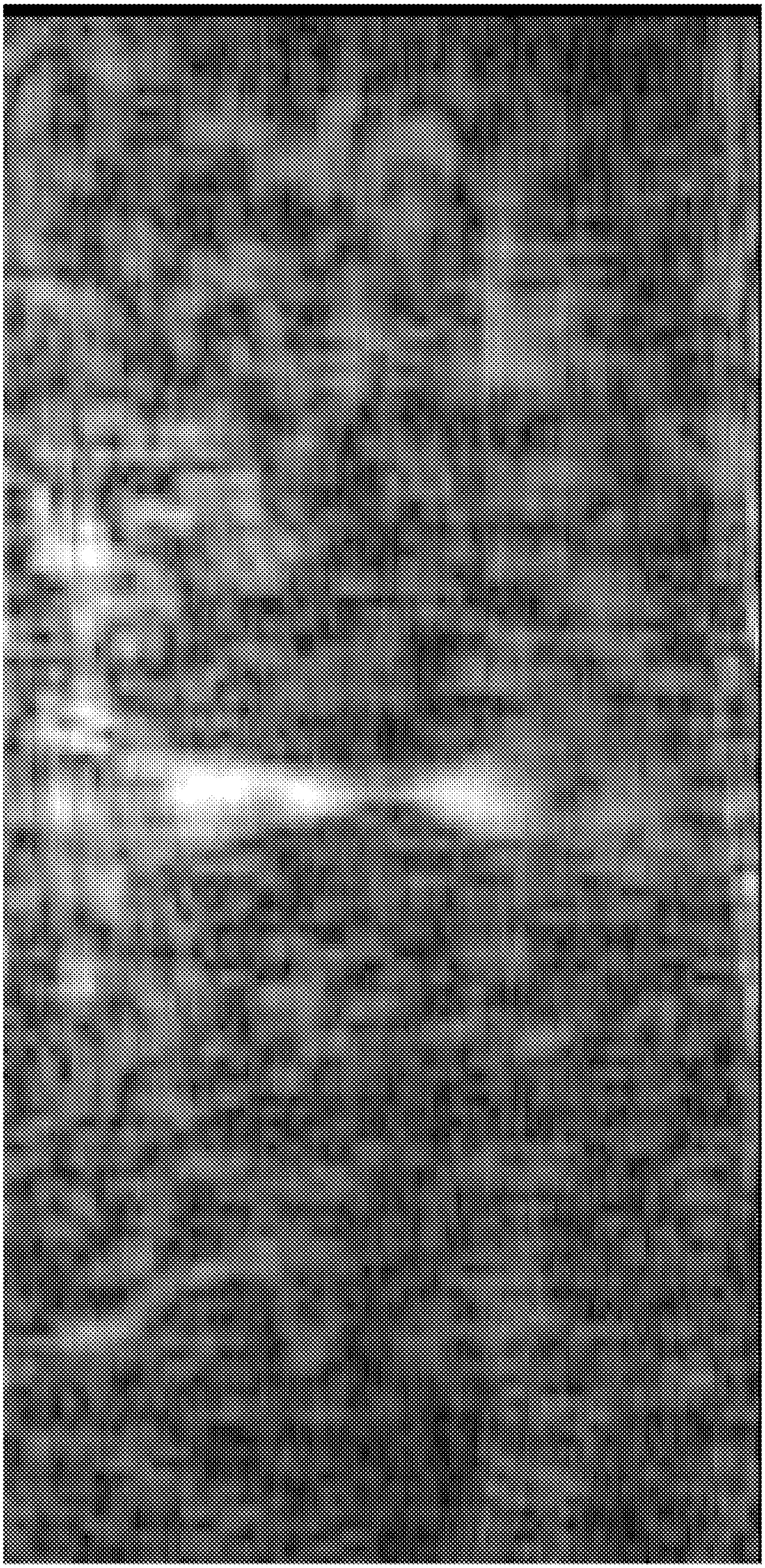
FIG. 25 illustrates an asynchronous resonance image of a needle tip double ringdown artifact acquired with a time delay of 80 microseconds.
Figure 26:
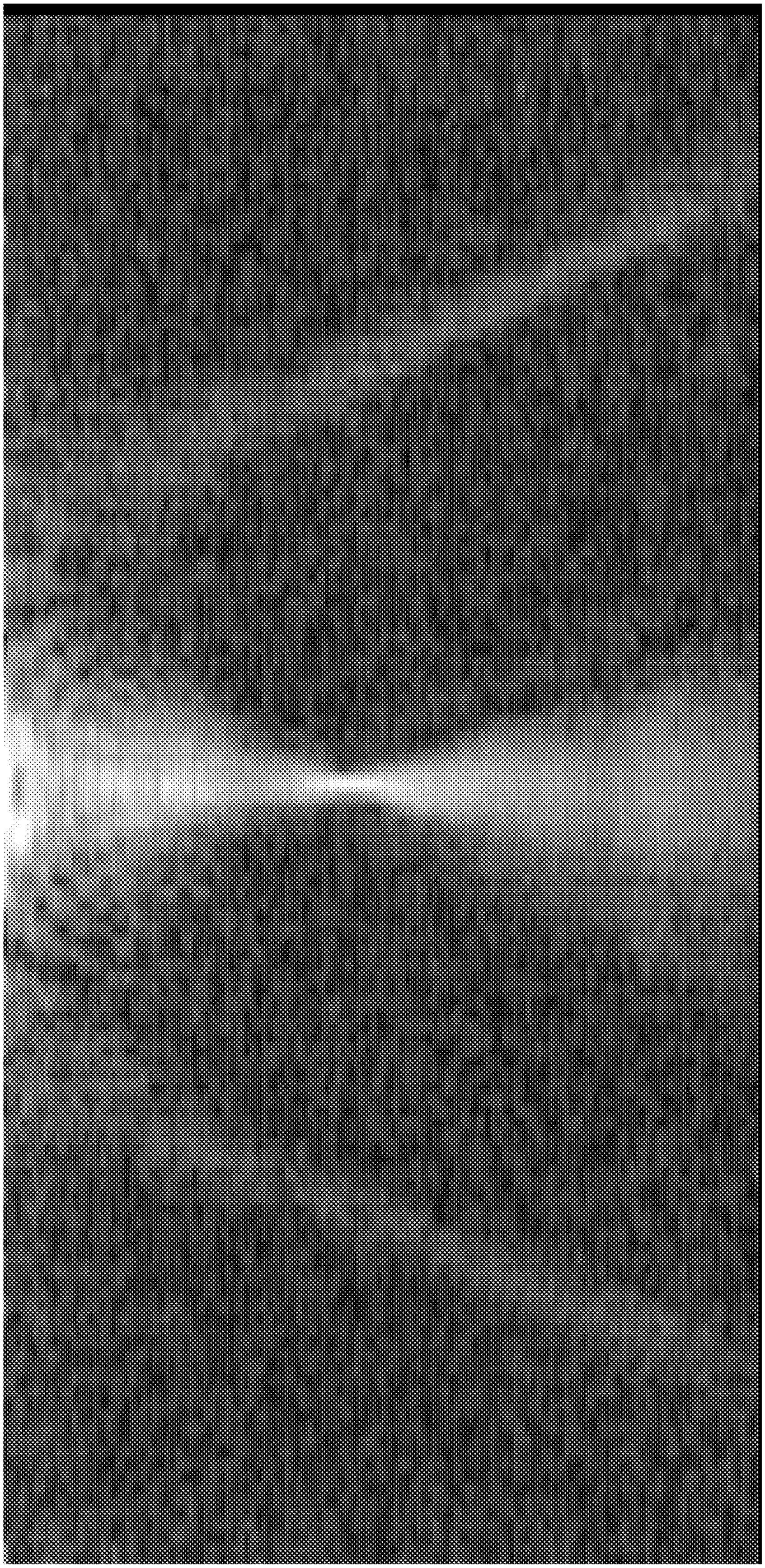
FIG. 26 illustrates an asynchronous resonance image of a needle tip double ringdown artifact acquired with a time delay of 180 microseconds.
Figure 27:
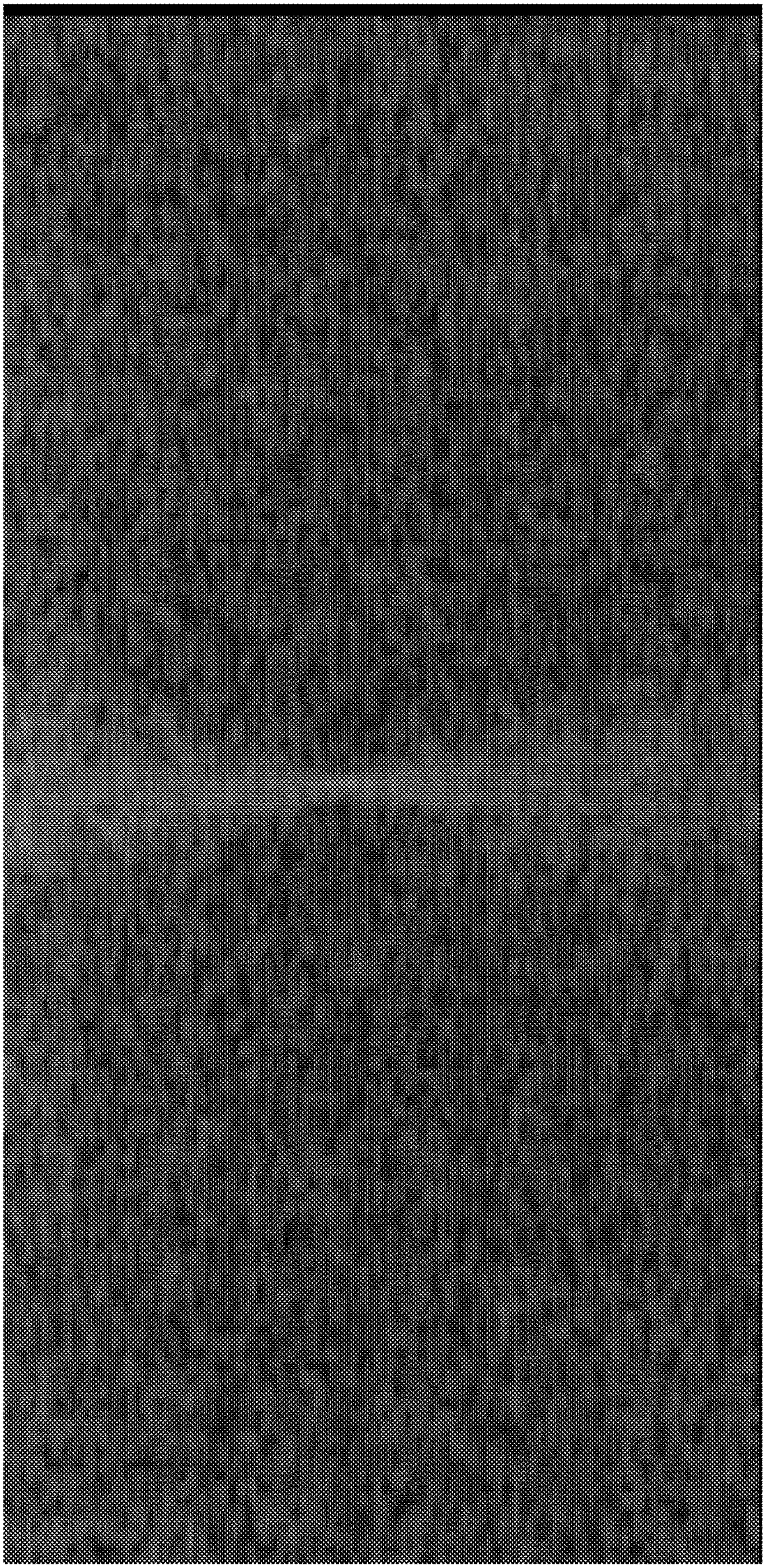
FIG. 27 illustrates an asynchronous resonance image of a needle tip double ringdown artifact acquired with a time delay of 400 microseconds.

The maximum conspicuity double ringdown artifact may be (e.g., usually) produced by the (e.g., shortest) time delay which does not result in visualization of tissue echoes. In one or more scenarios, a longer time delay may further improve double ringdown artifact conspicuity. A useful (e.g., optimal) time delay may be typically in the range of 40-500 microseconds and/or 100-400 mircoseconds. This range may vary with factors such as machine settings and/or soft tissue echogenicity. FIG. 25, FIG. 26, and FIG. 27 illustrate examples of images with time delays that are too short, optimal, and too long.

FIG. 25, FIG. 26, and FIG. 27 illustrate asynchronous resonance images of needle tip double ringdown artifacts acquired with varied time delays. FIG. 25 illustrates an asynchronous resonance image of a needle tip double ringdown artifact acquired with a time delay of 80 microseconds. This time delay may be too short, such that tissue echoes may obscure the double ringdown artifact. FIG. 26 illustrates an asynchronous resonance image of a needle tip double ringdown artifact acquired with a time delay of 180 microseconds. This time delay may be appropriate, such that double ringdown artifacts may be well visualized. FIG. 27 illustrates an asynchronous resonance image of a needle tip double ringdown artifact acquired with a time delay of 400 microseconds. This time delay may be too long, such that double ringdown artifacts may be weakly visualized.

In one or more scenarios, the conspicuity of the needle tip double ringdown artifact may be affected by the duration of the ultrasound transmit pulse. Standard B-mode ultrasound uses a short transmit pulse, e.g., 1 cycle, perhaps in order to optimize axial resolution, among other reasons. The conspicuity of the needle tip double ringdown artifact in asynchronous resonance imaging may be increased by using a longer duration transmit pulse, such as for example in the range of 5-25 cycles. A long duration transmit pulse may increase the energy delivered to the needle tip that may result in stronger double ringdown artifact echoes, perhaps without increasing the transmit pulse drive power, for example.

Figure 28:
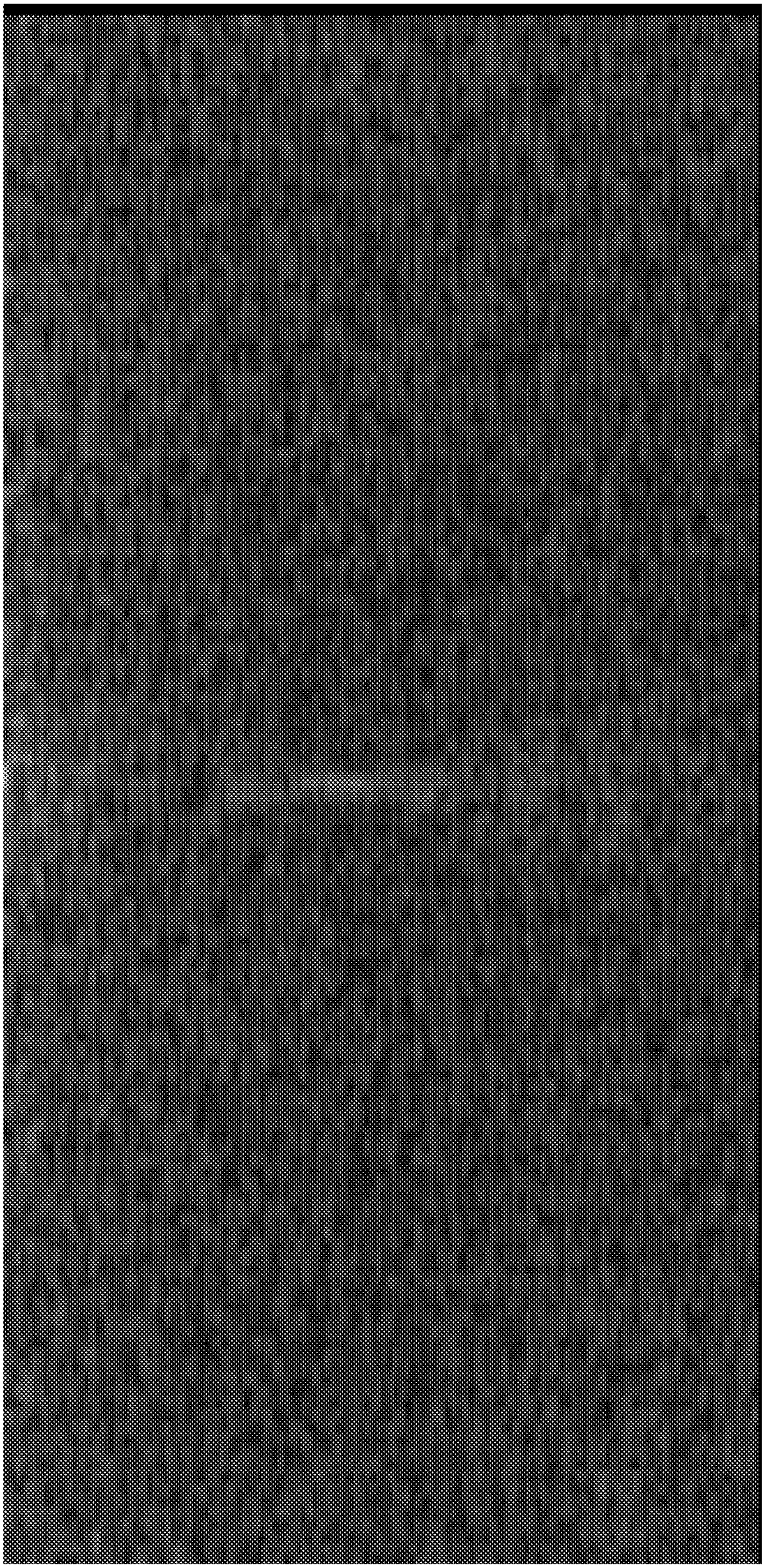
FIG. 28 illustrates an example needle tip asynchronous resonance image acquired with a pulse duration of 1 cycle.
Figure 29:
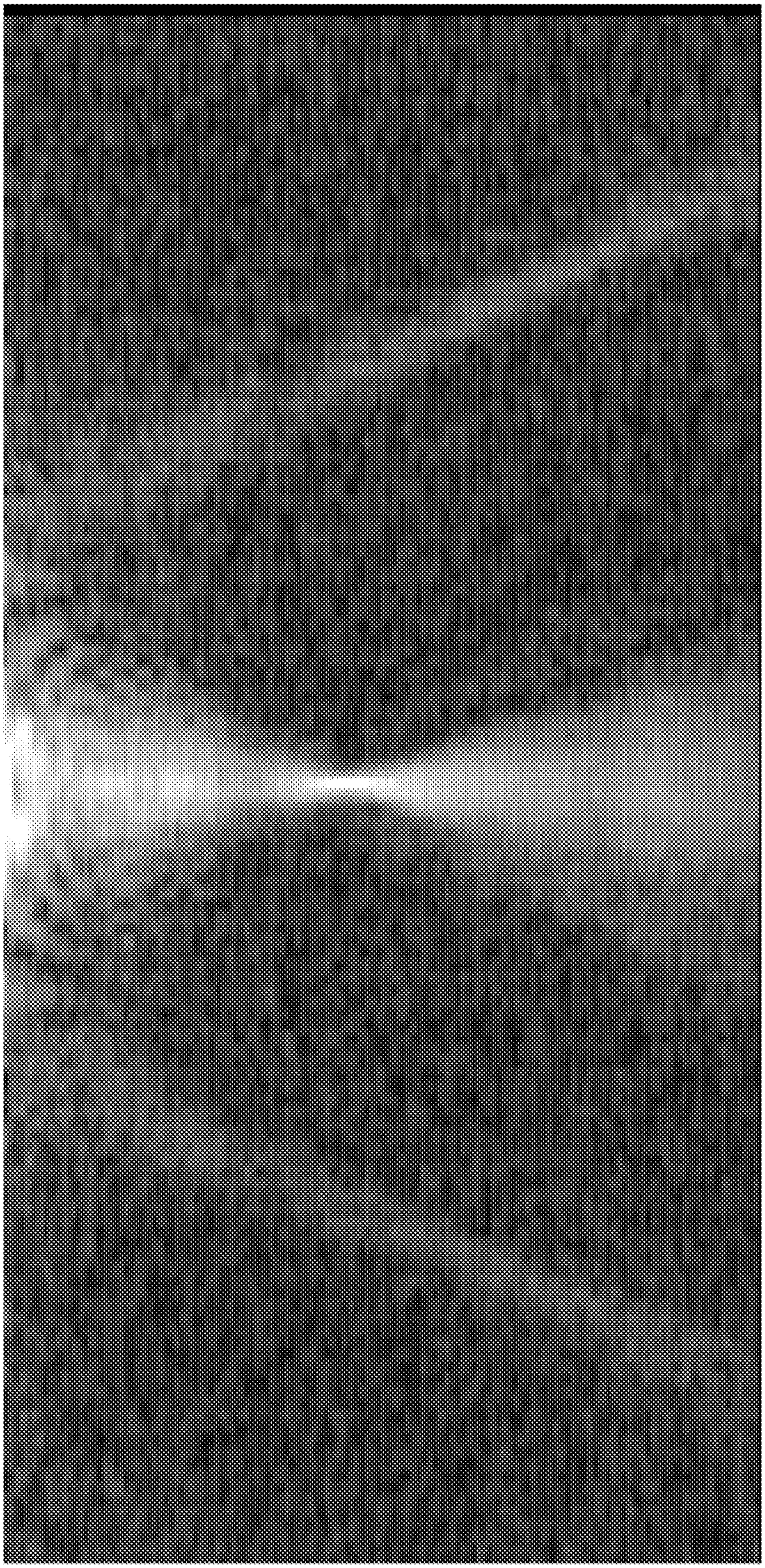
FIG. 29 illustrates an example needle tip asynchronous resonance image acquired with a pulse duration of 25 cycles.
Figure 30:
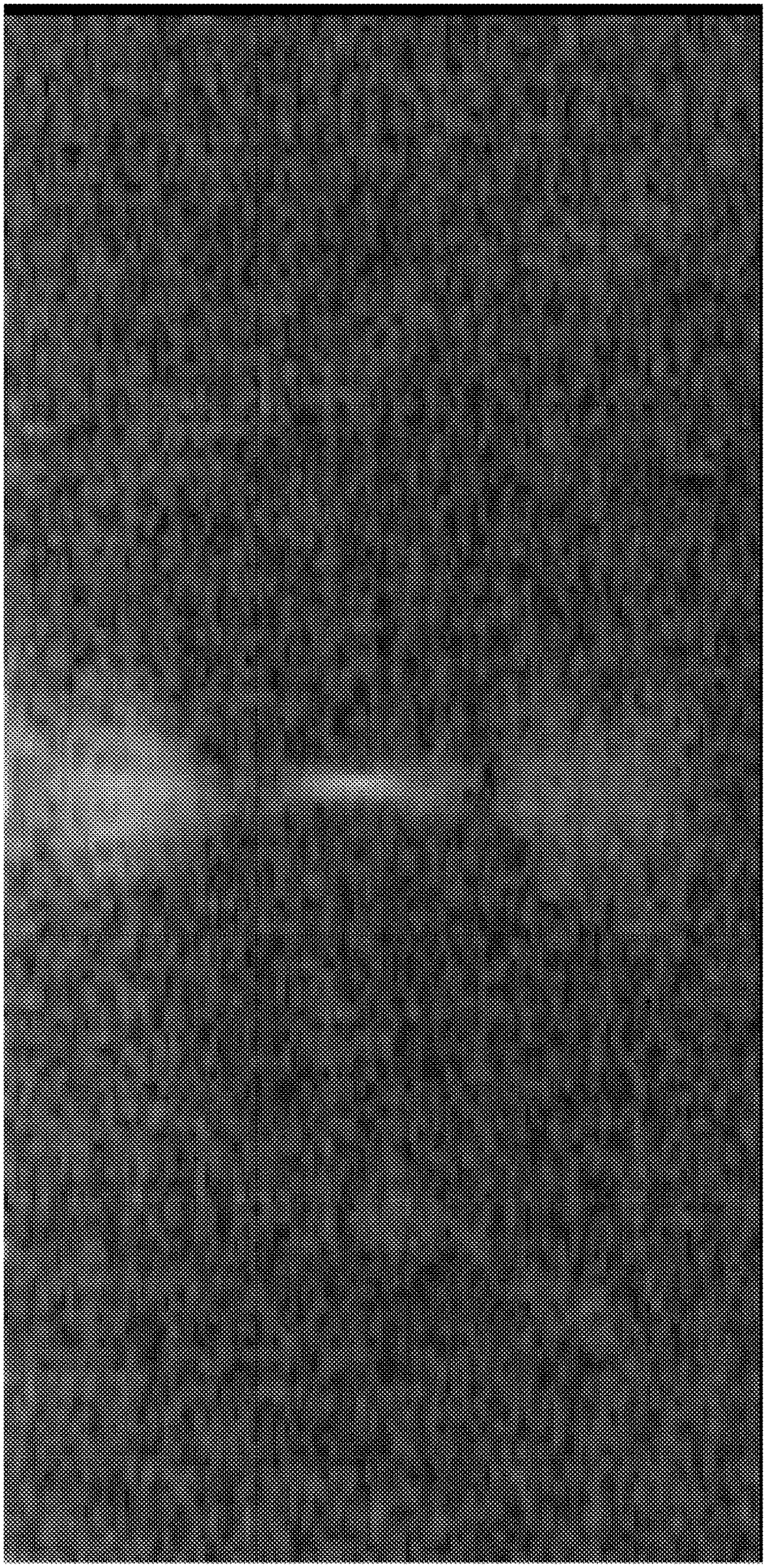
FIG. 30 illustrates an example needle tip asynchronous resonance image acquired with a pulse duration of 100 cycles.

The transmit pulse drive power may be limited by hardware factors and/or regulatory limits due to patient safety bioeffects concerns, among other reasons. Pulse bandwidth may be inversely proportional to pulse duration. A longer transmit pulse may result in a narrower bandwidth, perhaps allowing the transmit pulse energy to be more concentrated around the needle's resonant frequency. A pulse duration that may be too long may result in decreased double ringdown artifact conspicuity. FIG. 28, FIG. 29, and FIG. 30 illustrate examples of asynchronous resonance images acquired with varied pulse durations.

FIG. 28, FIG. 29, and FIG. 30 illustrate examples of needle tip asynchronous resonance images acquired with varied pulse durations. FIG. 28 illustrates an example needle tip asynchronous resonance image acquired with a pulse duration of 1 cycle. This duration may be too short, such that a double ringdown artifact may be poorly visualized. FIG. 29 illustrates an example needle tip asynchronous resonance image acquired with a pulse duration of 25 cycles. This duration may be appropriate, such that a double ringdown artifact may be well visualized. FIG. 30 illustrates an example needle tip asynchronous resonance image acquired with a pulse duration of 100 cycles. This duration may be too long, such that a double ringdown artifact may be poorly visualized.

Figure 31:
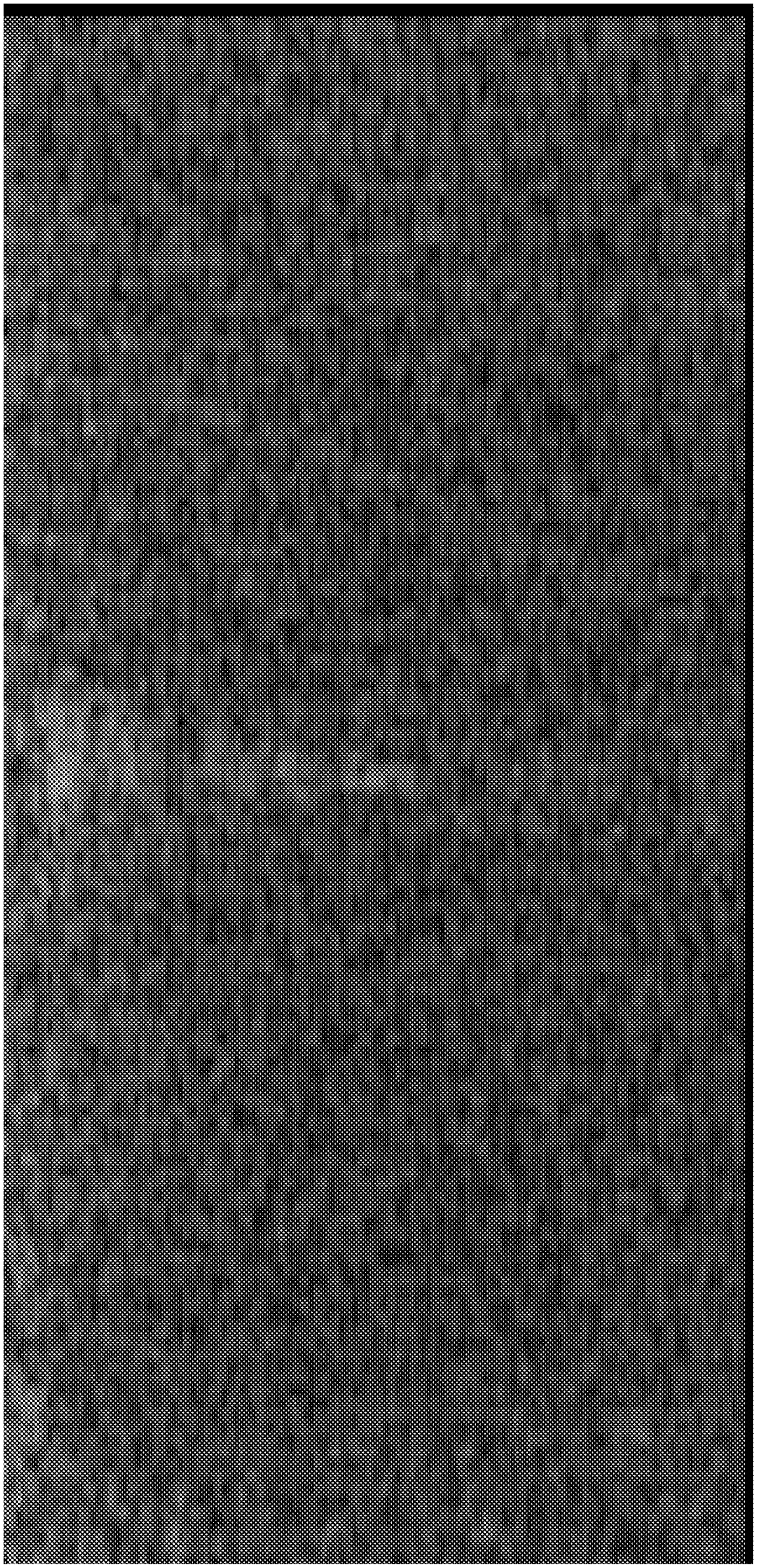
FIG. 31 illustrates a needle tip asynchronous resonance image obtained with a 5.00 megahertz center frequency transmit pulse.
Figure 32:
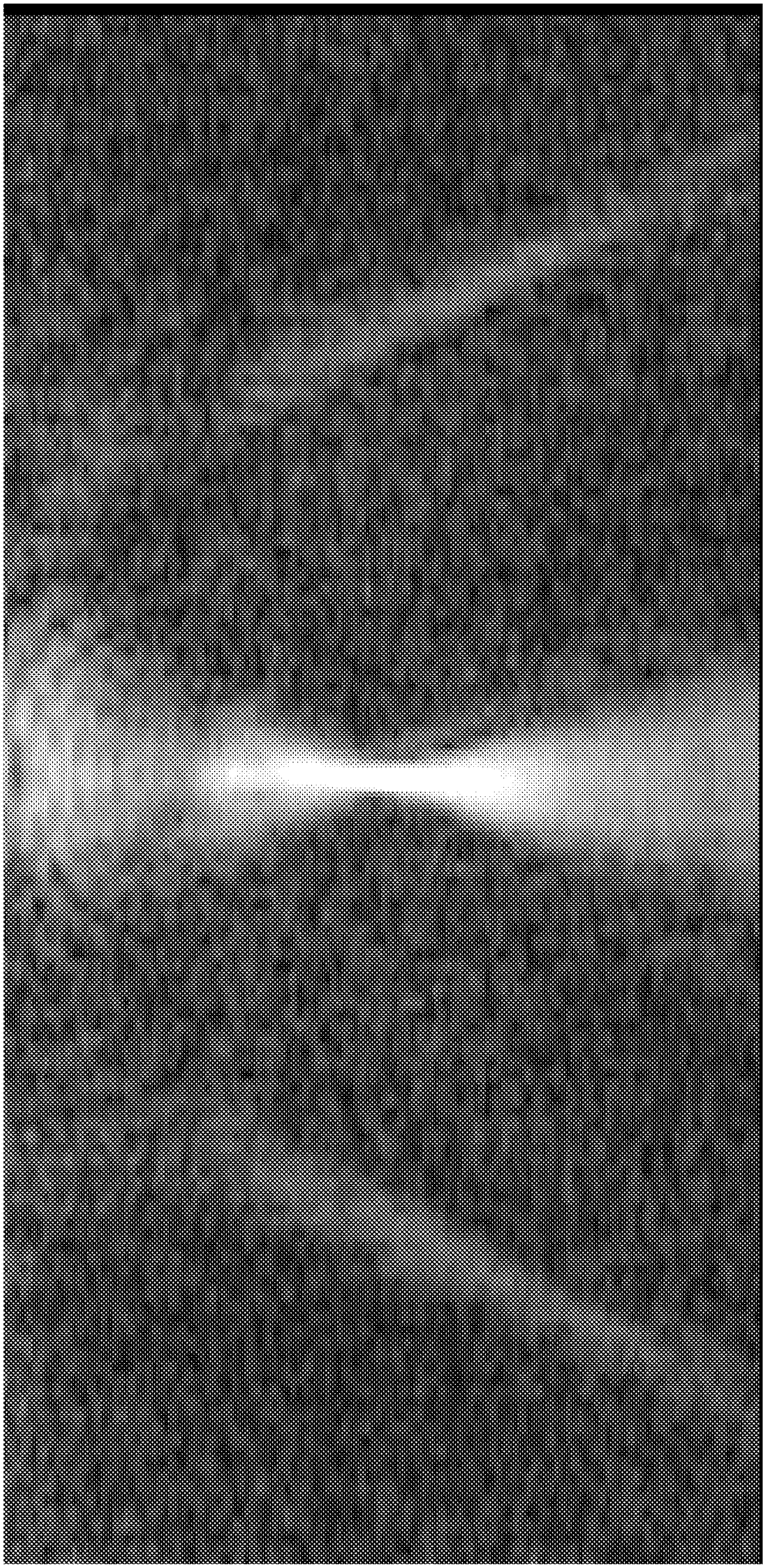
FIG. 32 illustrates a needle tip asynchronous resonance image obtained with a 5.43 megahertz center frequency transmit pulse.
Figure 33:
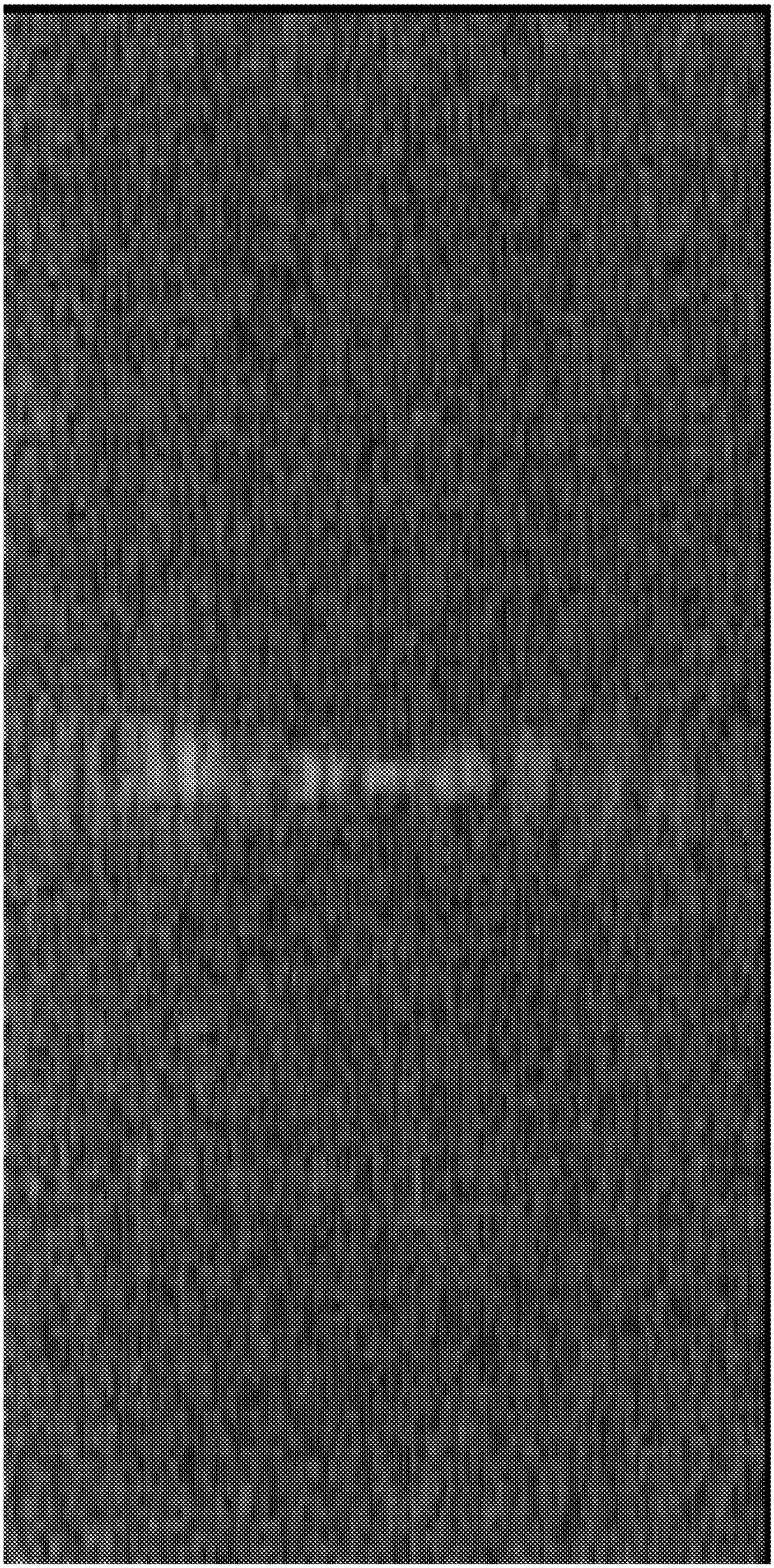
FIG. 33 illustrates a needle tip asynchronous resonance image obtained with a 6.58 megahertz center frequency transmit pulse.

A needle with a given set of properties, such as gauge, length, and material composition, may have a characteristic resonance frequency. Perhaps when the center frequency of the asynchronous resonance imaging transmit pulse matches the needle's resonance frequency, among other scenarios, the conspicuity of the needle tip double ringdown artifact may be maximized. FIG. 31, FIG. 32, and FIG. 33 illustrate examples of an intravenous catheter needle with a stainless steel hypodermic tubing 22 regular wall gauge canula with free length 2.56 inches, triple ground lancet A bevel, polymer hub, and 20 gauge catheter in place. This may produce a maximum intensity needle tip double ringdown artifact with an asynchronous resonance imaging transmit pulse center frequency of 5.43 megahertz. Transmit pulse center frequencies of 5.00 and 6.58 megahertz may produce reduced intensity double ringdown artifacts.

FIG. 31, FIG. 32, and FIG. 33 illustrate needle tip asynchronous resonance images obtained with varied transmit pulse center frequencies. There may be a 22 gauge intravenous catheter needle, with 20 gauge catheter in place, used to obtain the images. FIG. 31 illustrates a needle tip asynchronous resonance image obtained with a 5.00 megahertz center frequency transmit pulse. With this center frequency, a double ringdown artifact may be poorly visualized. FIG. 32 illustrates a needle tip asynchronous resonance image obtained with a 5.43 megahertz center frequency transmit pulse. With this center frequency, a double ringdown artifact may be well visualized. FIG. 33 illustrates a needle tip asynchronous resonance image obtained with a 6.58 megahertz center frequency transmit pulse. With this center frequency, a double ringdown artifact may be poorly visualized.

The first pulse center frequency may be adjusted to provide the most conspicuous double ringdown artifact. This may occur at approximately 5.4 MHz for a 22 Regular Wall Gauge hypodermic tubing needle with nominal outer diameter 0.718 millimeters and nominal inner diameter 0.413 millimeters. A first pulse center frequency much greater or less than this value, for example less than or equal to 5.0 MHz or greater than or equal to 5.9 MHz for a 22 Regular Wall Gauge hypodermic tubing needle, may result in a decreased conspicuity and/or absent double ringdown artifact.

The center frequency of the second pulse may be adjusted by the user/operator to create a better/best soft tissue image. The highest frequency that may still produce adequate penetration may produce the better/best soft tissue image. This may be determined by the user/operator on a patient-by-patient basis, such as is typical in B-mode medical ultrasonography.

In one or more scenarios, increasing the duration of the first pulse may result in increased conspicuity of the double ringdown artifact. A first pulse duration that is (e.g., too) long can decrease double ringdown artifact conspicuity. Good and/or sufficient double ringdown artifact conspicuity can be achieved with a pulse duration in the range of 1-25 cycles. The optimal first pulse duration may vary depending on machine settings and patient factors, for example.

In one or more scenarios, it may be useful (e.g., important) in asynchronous resonance imaging to use a time delay long enough to remove one or more, or all, tissue echoes so that they do not obscure the needle tip double ringdown artifact. In one or more scenarios, another strategy may include the use of a shorter time delay, in which some tissue echoes may still be present, and signal processing may be applied. A bandpass filter may be used to remove the tissue echoes so that the double ringdown artifact may be better visualized. This shorter time delay may increase the strength of the double ringdown artifact echoes, for example.

As the time delay from the ultrasound pulse to the start of the echo receive period is increased, the strength of the tissue echoes and the needle tip ringdown artifact echoes both may decrease. A more rapid decrease may occur for the tissue echoes. The double ringdown artifact may be (e.g., may usually be) best visualized with the shortest time delay that does not result in receiving tissue echoes. For example, best visualization may occur with the time delay resulting in the strongest ringdown artifact echoes with no competing tissue echoes. Perhaps for example, if the tissues echoes are strong and/or long lasting, among other scenarios, there can be a situation in which a time delay long enough to eliminate one or more, or all, tissue echoes may result in significant weakening of ringdown artifact echoes. This may result in poor visualization of the double ringdown artifact.

In such scenarios, among other scenarios, other strategies may include the use of a shorter time delay. This may increase the strength of the ringdown artifact echoes. The tissue echoes may be weakened but still may be present and may partially obscure ringdown artifact echoes. Application of a bandpass filter to the echoes may remove the tissue echoes and increase the visualization of the double ringdown artifact. The bandpass filter may (e.g., typically) have a center frequency 0%-20% higher than the transmit pulse center frequency, a −3 dB bandwidth of 10%-30% of the bandpass filter center frequency, and a −20 dB stopband of 30%-45% of the center frequency of the bandpass filter. For example, a transmit pulse with center frequency of 5.4 MHz could be combined with a bandpass filter with center frequency 5.9 MHz, −3 dB bandwidth 5.47-6.33 MHz, and −20 dB stopband 4.86-6.94 MHz.

Figure 34B:
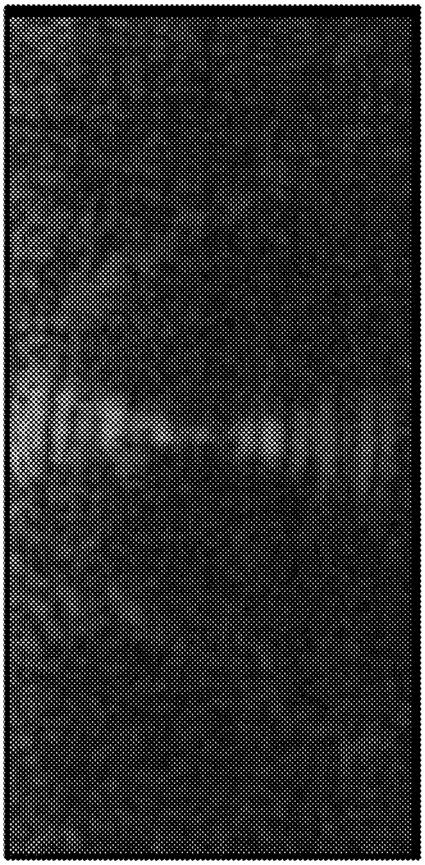
FIG. 34B illustrates an asynchronous resonance image with the use of a bandpass filter.
Figure 34A:
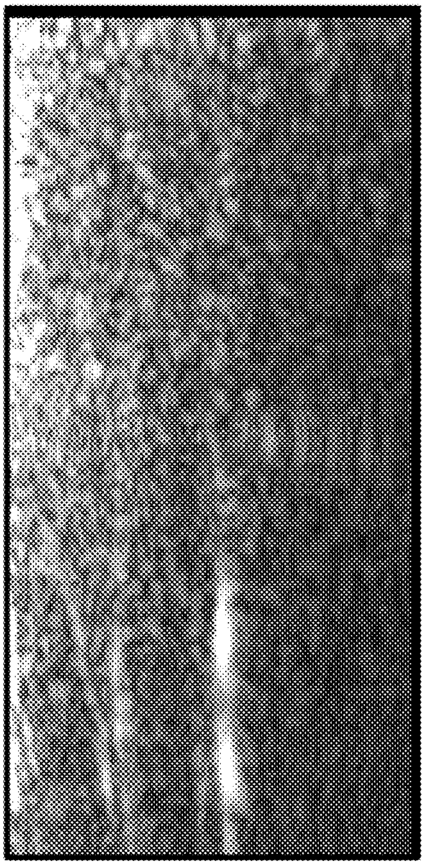
FIG. 34A illustrates an example needle tip asynchronous resonance image with too short a time delay.

FIG. 34A illustrates a needle tip asynchronous resonance image, with transmit pulse center frequency 5.00 megahertz, with too short a time delay, such that tissue echoes may partially obscure the double ringdown artifact. FIG. 34B illustrates an asynchronous resonance image, with transmit pulse center frequency 5.00 megahertz, with the same time delay as used to generate the image in FIG. 34A. A bandpass filter, with center frequency 6.00 megahertz, −3 decibel bandwidth 5.60-6.40 megahertz, −20 decibel stopband cut-off frequencies of 5.01 and 6.99 megahertz, may be applied in the FIG. 34B image generation that may provide for removal of one or more tissue echoes and/or may increase the conspicuity of double ringdown artifact(s).

Perhaps in order to optimize ultrasound needle tip guidance, among other reasons, a compound image may be created in which the double ringdown artifact(s) indicates the position of the needle tip in the standard B-mode image. B-mode and asynchronous resonance images may be acquired (e.g., separately). This may allow use of transmit pulse characteristics that may be optimized for the image type being acquired. A B-mode transmit pulse could be short, e.g., 1 cycle, for example to optimize axial resolution. For a 20 millimeter depth soft tissue image, for example, a higher center frequency may be used, e.g., 8.9 megahertz, that may optimize image resolution. An asynchronous resonance imaging transmit pulse could be longer, e.g., 20 cycles, for example to maximize double ringdown artifact conspicuity. A lower center frequency, e.g., 5.43 megahertz, may be used to match the resonance frequency of the needle, for example.

Figure 35:
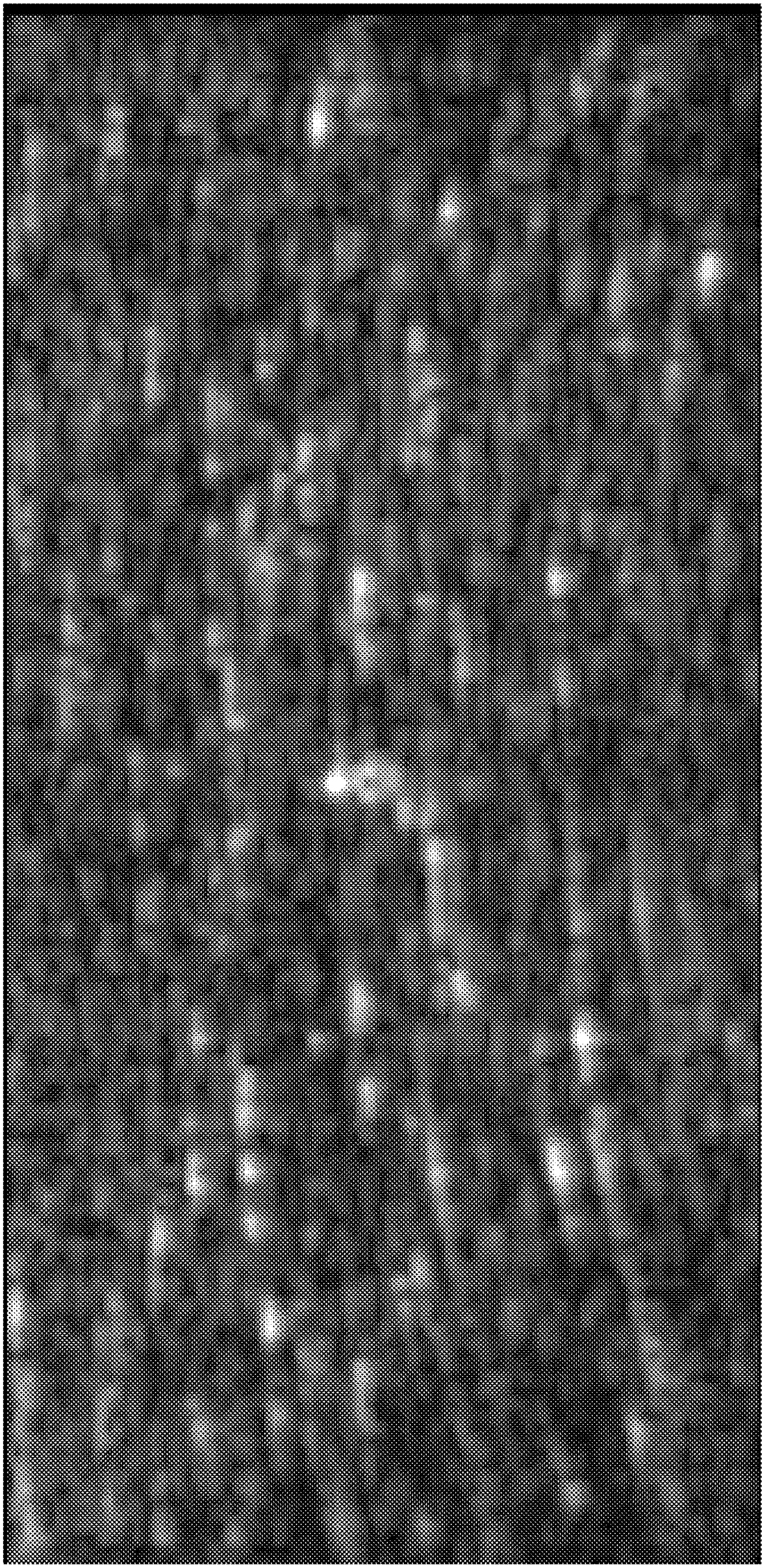
FIG. 35 illustrates an example of a B-mode technique image in which a needle tip is in the center of the image.
Figure 36:
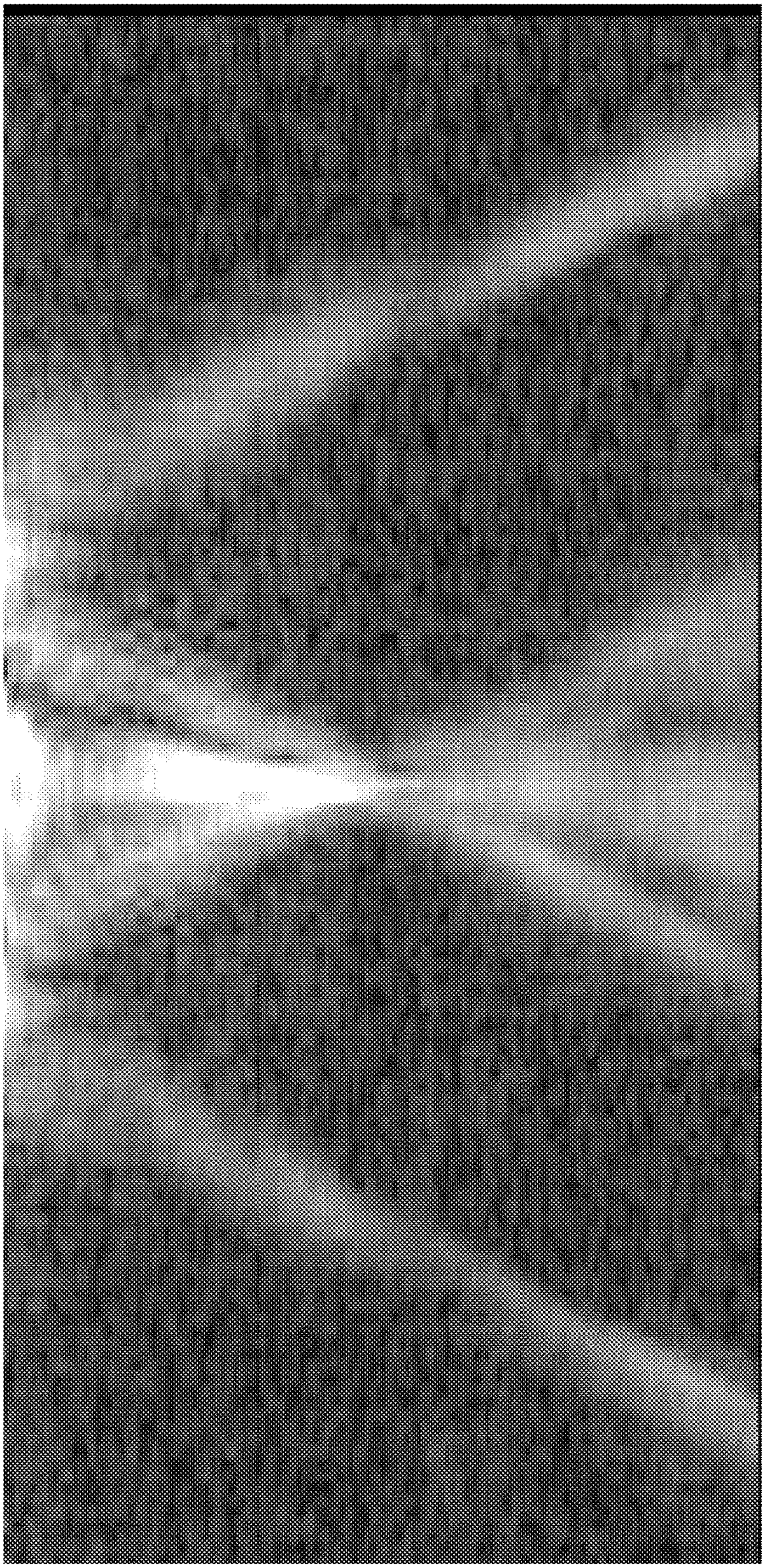
FIG. 36 illustrates an example of an asynchronous resonance image in which a needle tip double ringdown artifact is present.
Figure 37:
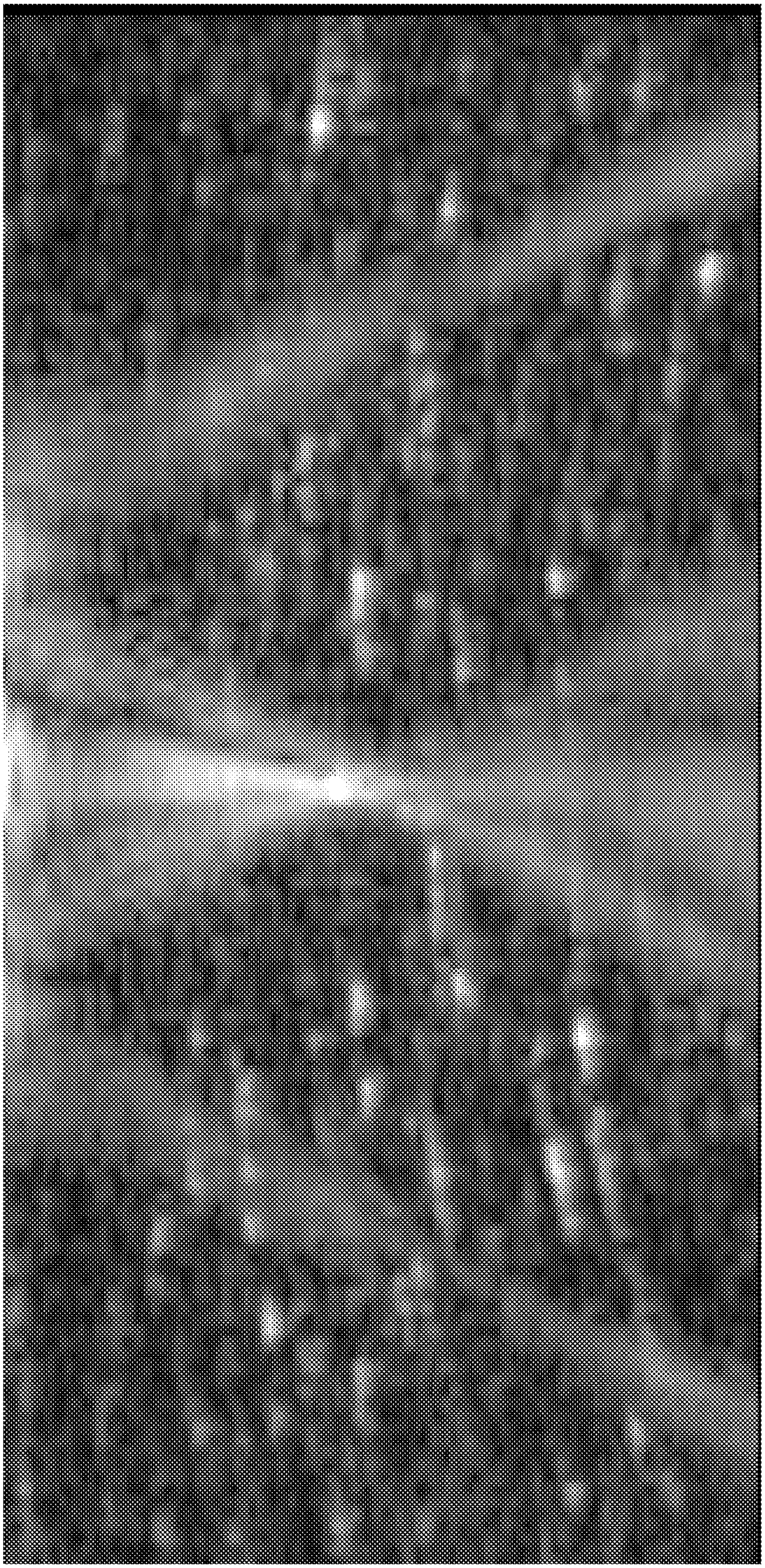
FIG. 37 illustrates an example of a compound image in which a needle tip position is indicated by the narrowest point of the double ringdown artifact.

In one or more scenarios, perhaps for example after the B-mode images and the asynchronous resonance images may be (e.g., separately) acquired. These images may be combined to create a compound image. FIG. 35, FIG. 36, and FIG. 37 illustrate an example of the creation of a compound image. FIG. 35 illustrates an example of a B-mode technique image in which a needle tip is in the center of the image. FIG. 36 illustrates an example of an asynchronous resonance image in which a needle tip double ringdown artifact is present. FIG. 37 illustrates an example of a compound image in which a needle tip position is indicated by the narrowest point of the double ringdown artifact.

In one or more scenarios, a compound image may be created using separate transmit pulses for dedicated B-mode image acquisitions and for asynchronous resonance image acquisitions. In one or more scenarios, another strategy may include the use a single transmit pulse to acquire both the B-mode images and the asynchronous resonance images. At least one advantage to obtaining both images from the same transmit pulse is an increased frame rate, which may be useful for focused pulse asynchronous resonance imaging, which may be hindered by a low frame rate.

A potential disadvantage of acquiring both B-mode and asynchronous resonance images from the same transmit pulse is that the (e.g., optimal) transmit pulse characteristics for B-mode and asynchronous resonance imaging could be different. Acquiring both B-mode and asynchronous resonance images with the same transmit pulse may result in using suboptimal pulse characteristics for one or both image types.

Figure 38:
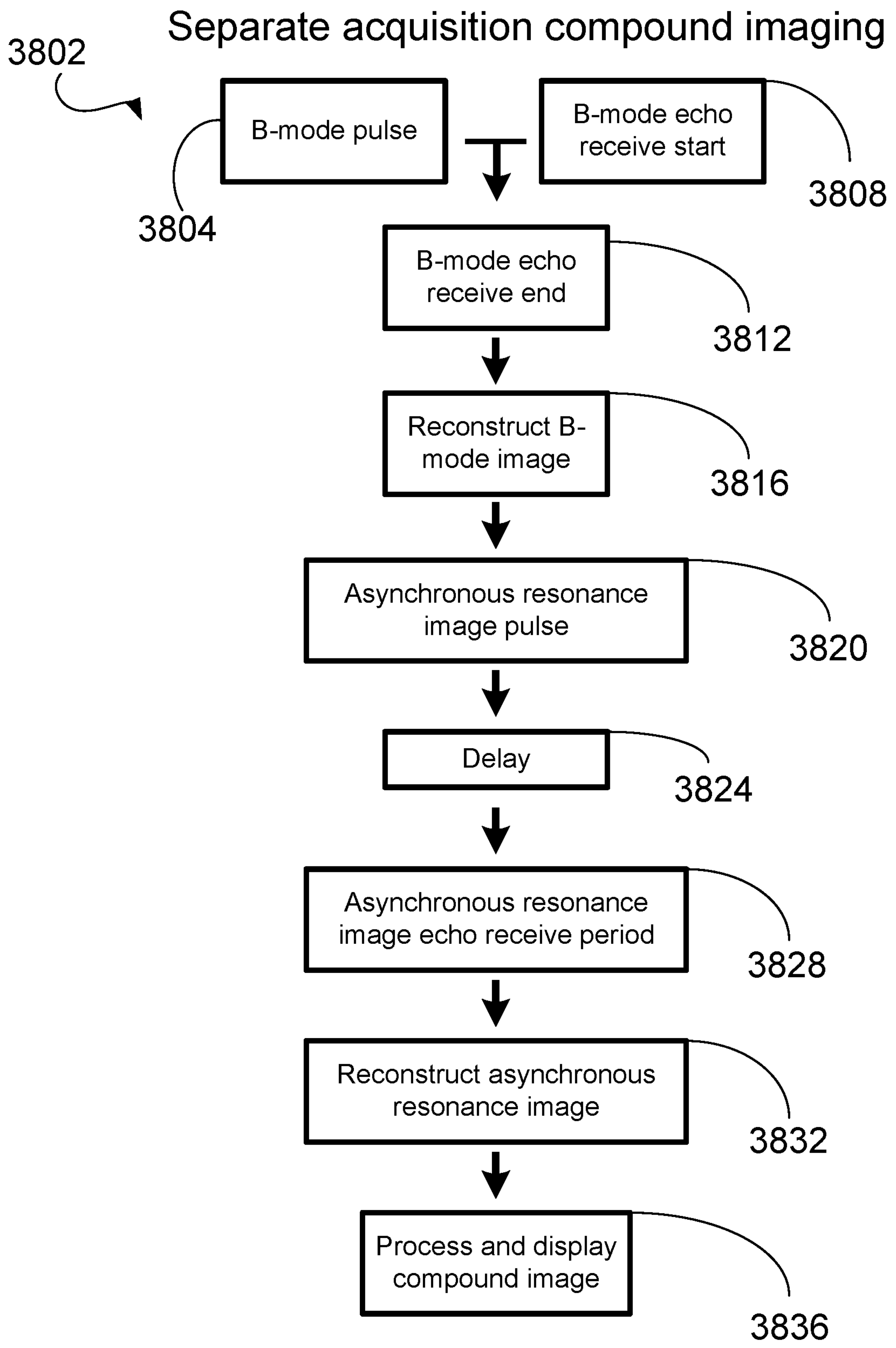
FIG. 38 illustrates a block diagram of an example compound imaging sequence using a separate image acquisition strategy.

FIG. 38 illustrates a block diagram of an example compound imaging sequence/technique 3802 using a separate image acquisition strategy. At 3804, a B-mode pulse may be generated/transmitted into target tissue. At 3808, receipt of B-mode echo signals may begin. At 3812, receipt of B-mode echo signals may end. At 3816, a B-mode image may be constructed/reconstructed based on the received B-mode echo signals/pulses. At 3820, an asynchronous resonance image (ARI) pulse may be generated/transmitted into the target tissue. At 3824, a (e.g., predetermined and/or user adjustable) time delay may be observed before any ARI echo signals may be received. At 3828, an ARI image echo signal receive period may begin. At 3832, an ARI image may be constructed/reconstructed based on the received ARI echo signals. At 3836, a compound image (e.g., based on the ARI images and the B-mode images) may be processed and displayed.

Figure 39:
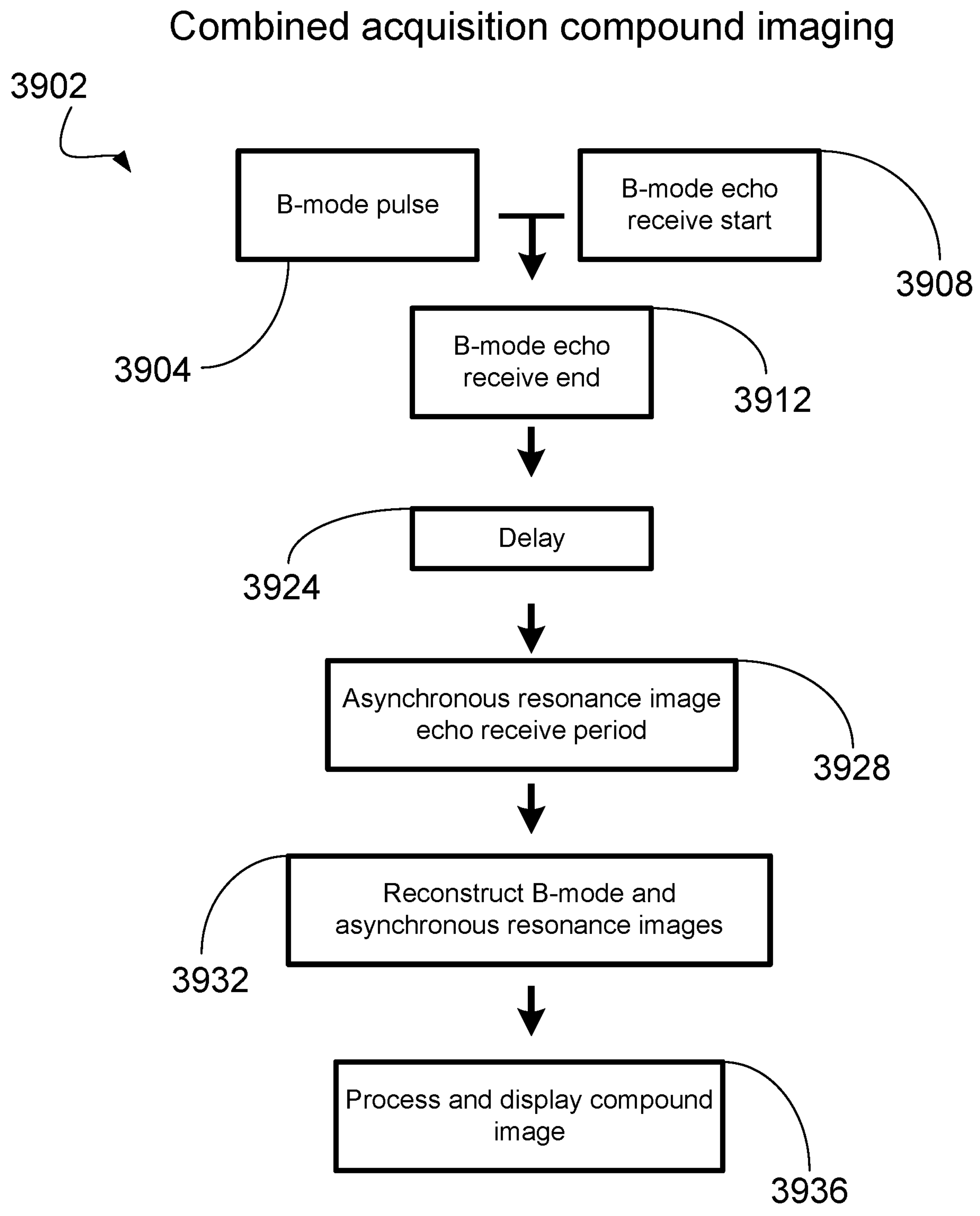
FIG. 39 illustrates a block diagram of an example combined imaging sequence using a combined image acquisition strategy.

FIG. 39 illustrates a block diagram of an example combined imaging sequence/technique 3902 using a combined image acquisition strategy. At 3904, a B-mode pulse may be generated/transmitted into target tissue. At 3908, receipt of B-mode echo signals may begin. At 3912, receipt of B-mode echo signals may end. At 3924, a (e.g., predetermined and/or user adjustable) time delay may be observed before any asynchronous resonance image (ARI) echo signals may be received. At 3928, an ARI image echo signal receive period may begin. At 3932, an ARI image(s) and B-mode image(s) may be constructed/reconstructed based on the received echo signals. At 3936, a compound image (e.g., based on the ARI images and the B-mode images) may be processed and displayed.

In one or more scenarios, an imaging probe/transducer of an ultrasound scanner/scanning device may transmit one or more ultrasound pulses. For a period of time after the pulse generation has started, during which the transducer does not listen for echoes (e.g., for a predetermined and/or adjustable time delay). After the period of time expires, the transducer may start to listen for echoes. The scanning device may perform/enter an echo/receive period that may correlate to a depth of image to be reconstructed. The scanning device may reconstruct the echoes to make an image. Perhaps if a needle tip is present, a double ringdown artifact may be seen on the image/display. The scanning device may carry out standard ultrasound scanning and/or present a (e.g., compound) image on a display.

Figure 4:
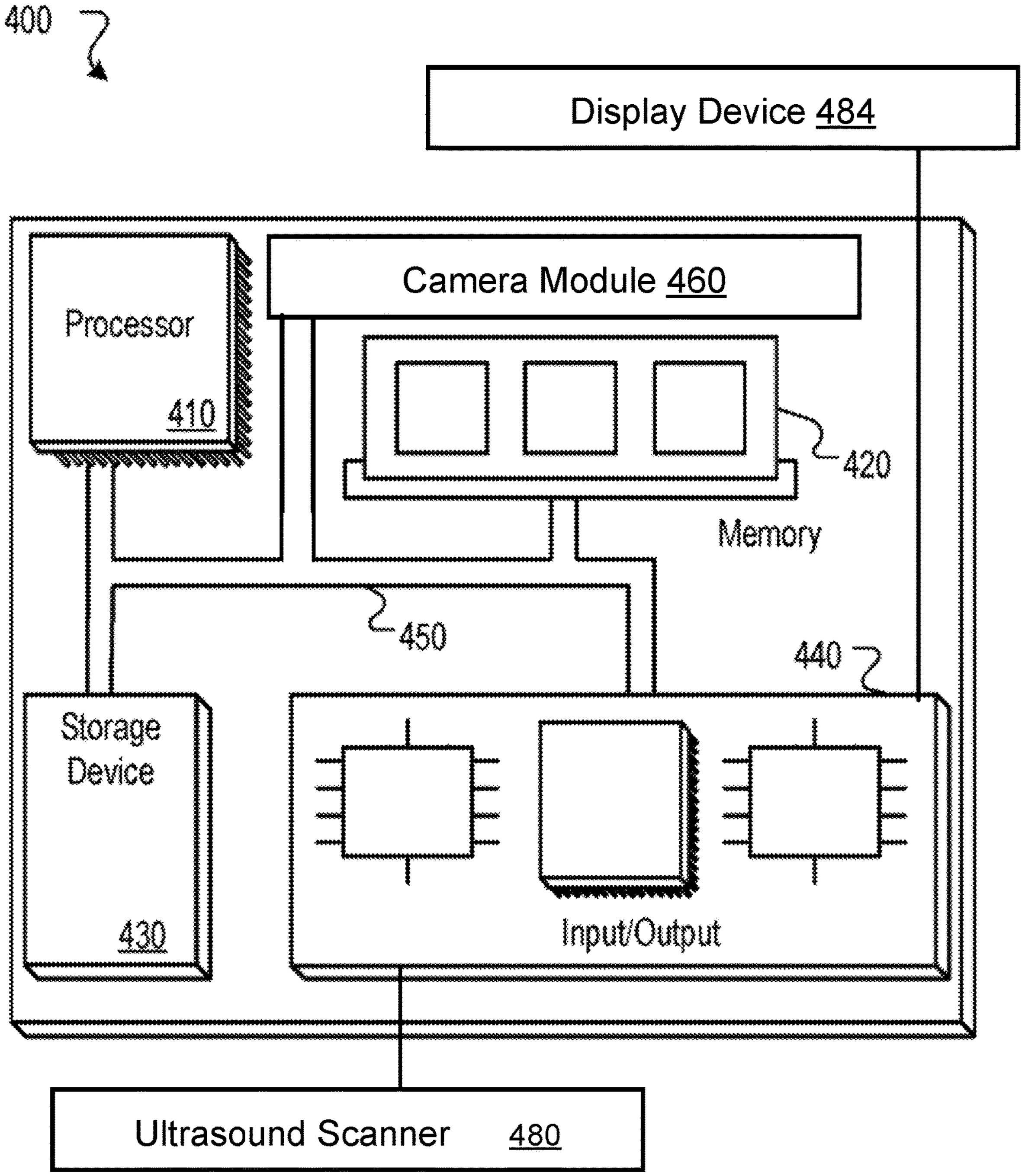
FIG. 4 is a block diagram of a hardware configuration of an example device that may control one or more ultrasound devices described herein.

FIG. 4 is a block diagram of a hardware configuration of an example device that may function as a process control device/logic controller for any of the ultrasound scanners described herein and/or for any of the ultrasound scanner processing/techniques disclosed herein may be conducted. The hardware configuration 400 may be in wired and/or wireless communication, and/or in Internet/cloud communication, with any of the ultrasound scanner systems/devices described herein. The hardware configuration 400 may be operable to facilitate delivery of information from an internal server of a device. The hardware configuration 400 can include a processor 410, a memory 420, a storage device 430, and/or an input/output device 440. One or more of the components 410, 420, 430, and 440 can, for example, be interconnected using a system bus 450. The processor 410 can process instructions for execution within the hardware configuration 400. The processor 410 can be a single-threaded processor or the processor 410 can be a multi-threaded processor. The processor 410 can be capable of processing instructions stored in the memory 420 and/or on the storage device 430.

The memory 420 can store information within the hardware configuration 400. The memory 420 can be a computer-readable medium (CRM), for example, a non-transitory CRM. The memory 420 can be a volatile memory unit, and/or can be a non-volatile memory unit.

The storage device 430 can be capable of providing mass storage for the hardware configuration 400. The storage device 430 can be a computer-readable medium (CRM), for example, a non-transitory CRM. The storage device 430 can, for example, include a hard disk device, an optical disk device, flash memory and/or some other large capacity storage device. The storage device 430 can be a device external to the hardware configuration 400.

The input/output device 440 may provide input/output operations for the hardware configuration 400. The input/output device 440 (e.g., a transceiver device) can include one or more of a network interface device (e.g., an Ethernet card), a serial communication device (e.g., an RS-232 port), one or more universal serial bus (USB) interfaces (e.g., a USB 2.0 port) and/or a wireless interface device (e.g., an 802.11 card). The input/output device can include driver devices configured to send communications to, and/or receive communications from one or more networks. The input/output device 440 may be in communication with at least one display device 484. The display device 484 may display any of the ultrasound generated images described herein.

The input/output device 400 may be in communication with one or more input/output modules (not shown) that may be proximate to the hardware configuration 400 and/or may be remote from the hardware configuration 400. The one or more output modules may provide input/output functionality in the digital signal form, discrete signal form, TTL form, analog signal form, serial communication protocol, fieldbus protocol communication and/or other open or proprietary communication protocol, and/or the like.

The camera module 460 may provide digital video input/output capability for the hardware configuration 400. The camera module 460 may communicate with any of the elements of the hardware configuration 400, perhaps for example via system bus 450. The camera module 460 may capture digital images and/or may scan images of various kinds, such as Universal Product Code (UPC) codes and/or Quick Response (QR) codes, for example, among other images as described herein. For example, a subject's/patient's record may be accessible via a QR code, or the like. The camera module 460 may scan the subject/patient record QR code to access a subject's/patient's (e.g., medical) record such that one or more of the ultrasound images described herein may be (e.g., electronically) added to the subject's/patient's medical record.

The camera module 460 may include at least one microphone device and/or at least one speaker device (not shown). The camera module 460 may be in wired and/or wireless communication with the hardware configuration 400. In one or more scenarios, the camera module 460 may be external to the hardware configuration 400. In one or more scenarios, the camera module 460 may be internal to the hardware configuration 400.

An ultrasound scanner 480 may be in wired and/or wireless communication with the hardware configuration 400. The ultrasound scanner 480 may be any one of ultrasound scanners capable of providing/configured to provide at least the ultrasound probing and/or imaging as described herein.

Figure 40:
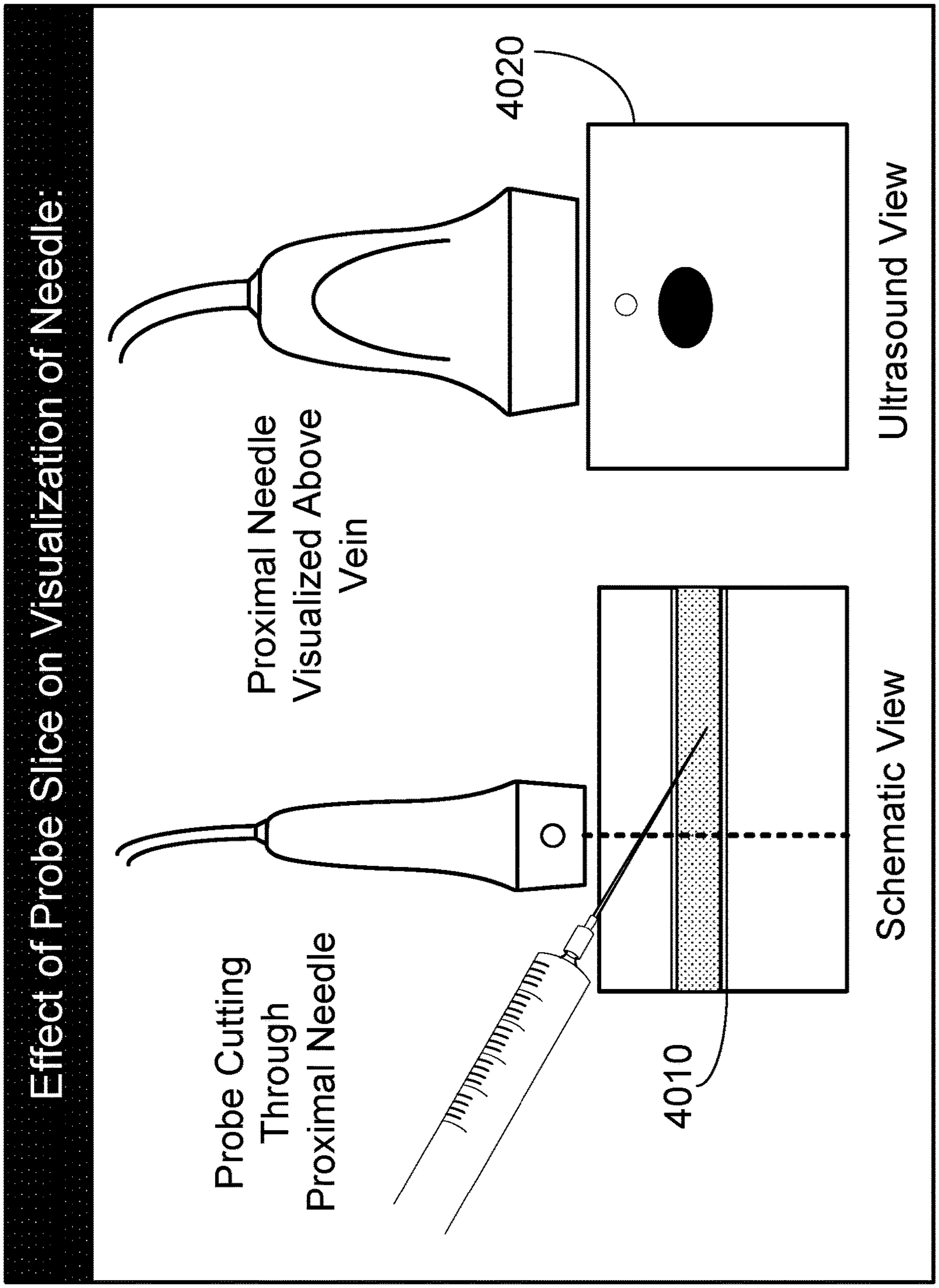
FIG. 40 illustrates an example of a depiction of the effect of a probe slice on the visualization of an inserted needle.

FIG. 40 illustrates an example of a depiction of the effect of a probe slice on the visualization of an inserted needle. At 4010, a schematic view of an imaging probe cutting through proximal needle insertion into tissue is illustrated. At 4020, an ultrasound view of a proximal needle visualized above a vein is illustrated. One or more techniques described herein may facilitate the detection of the needle tip while inserted in the tissue.

The subject matter of this disclosure, and components thereof, can be realized by instructions that upon execution cause one or more processing devices to carry out the processes and/or functions described herein. Such instructions can, for example, comprise interpreted instructions, such as script instructions, e.g., JavaScript or ECMAScript instructions, or executable code, and/or other instructions stored in a computer readable medium.

Implementations of the subject matter and/or the functional operations described in this specification and/or the accompanying figures can be provided in digital electronic circuitry, in computer software, firmware, and/or hardware, including the structures disclosed in this specification and their structural equivalents, and/or in combinations of one or more of them. The subject matter described in this specification can be implemented as one or more computer program products, e.g., one or more modules of computer program instructions encoded on a tangible program carrier for execution by, and/or to control the operation of, data processing apparatus.

A computer program (also known as a program, software, software application, script, or code) can be written in any form of programming language, including compiled or interpreted languages, and/or declarative or procedural languages. It can be deployed in any form, including as a stand-alone program or as a module, component, subroutine, and/or other unit suitable for use in a computing environment. A computer program may or might not correspond to a file in a file system. A program can be stored in a portion of a file that holds other programs and/or data (e.g., one or more scripts stored in a markup language document), in a single file dedicated to the program in question, and/or in multiple coordinated files (e.g., files that store one or more modules, sub programs, or portions of code). A computer program can be deployed to be executed on one computer or on multiple computers that may be located at one site or distributed across multiple sites and/or interconnected by a communication network.

The processes and/or logic flows described in this specification and/or in the accompanying figures may be performed by one or more programmable processors executing one or more computer programs to perform functions by operating on input data and/or generating output, thereby tying the process to a particular machine (e.g., a machine programmed to perform the processes described herein). The processes and/or logic flows can also be performed by, and apparatus can also be implemented as, special purpose logic circuitry, e.g., an FPGA (field programmable gate array) and/or an ASIC (application specific integrated circuit).

Computer readable media suitable for storing computer program instructions and/or data may include all forms of non-volatile memory, media and memory devices, including by way of example semiconductor memory devices (e.g., EPROM, EEPROM, and/or flash memory devices); magnetic disks (e.g., internal hard disks or removable disks); magneto optical disks; and/or CD ROM and DVD ROM disks. The processor and/or the memory can be supplemented by, or incorporated in, special purpose logic circuitry.

While this specification and the accompanying figures contain many specific implementation details, these should not be construed as limitations on the scope of any invention and/or of what may be claimed, but rather as descriptions of features that may be specific to described example implementations. Certain features that are described in this specification in the context of separate implementations can also be implemented in combination in perhaps one implementation. Various features that are described in the context of perhaps one implementation can also be implemented in multiple combinations separately or in any suitable subcombination. Although features may be described above as acting in certain combinations and/or perhaps even (e.g., initially) claimed as such, one or more features from a claimed combination can in some cases be excised from the combination. The claimed combination may be directed to a sub-combination and/or variation of a sub-combination.

While operations may be depicted in the drawings in an order, this should not be understood as requiring that such operations be performed in the particular order shown and/or in sequential order, and/or that all illustrated operations be performed, to achieve useful outcomes. The described program components and/or systems can generally be integrated together in a single software product and/or packaged into multiple software products.

Examples of the subject matter described in this specification have been described. The actions recited in the claims can be performed in a different order and still achieve useful outcomes, unless expressly noted otherwise. For example, the processes depicted in the accompanying figures do not require the particular order shown, and/or sequential order, to achieve useful outcomes. Multitasking and parallel processing may be advantageous in one or more scenarios.

While the present disclosure has been illustrated and described in detail in the drawings and foregoing description, the same is to be considered as illustrative and not restrictive in character, it being understood that only certain examples have been shown and described, and that all changes and modifications that come within the spirit of the present disclosure are desired to be protected.

What is claimed is:

1. A method performed by an ultrasound scanner, the ultrasound scanner having an imaging probe, the method comprising: a) performing, by the ultrasound scanner, a target object detection process, the target object detection process comprising: a-i) transmitting, by the imaging probe, at a first time, one or more ultrasonic first pulse signals, the one or more ultrasonic first pulse signals configured to cause one or more first echo signals to be produced by adjacent tissue and a target object within the tissue; a-ii) receiving, by the imaging probe, upon reaching a second time that is subsequent to the first time by a predetermined delay period, the one or more first echo signals from the target object; and a-iii) generating, by the ultrasound scanner, target object image data corresponding to a location of the target object based on the one or more first echo signals; b) performing, by the ultrasound scanner, a tissue detection process, the tissue detection process comprising: b-i) transmitting, via the imaging probe, one or more ultrasonic second pulse signals, the one or more ultrasonic second pulse signals configured to cause one or more second echo signals to be produced by the adjacent tissue and the target object within the tissue; b-ii) receiving, at the imaging probe, the one or more second echo signals from the adjacent tissue; and b-iii) generating, by the ultrasound scanner, tissue image data corresponding to the adjacent tissue based on the one or more second echo signals; c) generating, by the ultrasound scanner, a compound image that includes a visual indicator of the location of the target object with respect to the tissue based on the target object image data and the tissue image data, wherein the visual indicator of the location of the target object is a double ringdown artifact that comprises: a top ringdown artifact propagating from the location of the target object towards the top of the compound image; and a bottom ringdown artifact propagating from the location of the target object towards the bottom of the compound image; and d) displaying, by the ultrasound scanner, the compound image on a display.

2. The method of claim 1, wherein, in the target object detection process, the first echo signals are not received between the first time and the second time.

3. The method of claim 1, wherein a narrowest point of the top ringdown artifact and a narrowest point of the bottom ringdown artifact each correspond to the location of the target object.

4. The method of claim 1, wherein the predetermined delay period is a value within a range of 40 to 500 microseconds.

5. The method of claim 1, wherein the predetermined delay period is a value within a range of 100 to 400 microseconds.

6. The method of claim 1, wherein the predetermined delay period is relatively short such that the one or more second echo signals from the adjacent tissue partly obscure the double ringdown artifact, and wherein an appearance of the one or more second echo signals from the adjacent tissue in the compound image is removed using signal processing.

7. The method of claim 1, wherein the target object detection process comprises applying a gain to the received first echo signals that is greater than any gain applied to the one or more second echo signals of the tissue detection process.

8. The method of claim 1, wherein, for the target object detection process:

the first pulse signals are focused pulse signals; and at least one of the elements a-i), or a-ii), is repeated one or more times.

9. The method of claim 1, wherein the target object detection process is repeated one or more times before carrying out the tissue detection process, wherein the target object image radiofrequency data is accumulated and averaged, and wherein the generation of the compound image is based on the accumulated and averaged target object image radiofrequency data.

10. The method of claim 1, wherein during the predetermined delay period the one or more first echo signals produced by the adjacent tissue dissipate and the one or more first echo signals produced by the target object persist.

11. A method performed by an ultrasound scanner, the ultrasound scanner having an imaging probe, the method comprising: a) transmitting, by the imaging probe, at a first time, one or more ultrasonic pulse signals, the one or more ultrasonic pulse signals configured to cause one or more echo signals to be produced by adjacent tissue and a needle within the tissue; b) performing, by the ultrasound scanner, a needle tip detection process, the needle tip detection process comprising: b-i) receiving, by the imaging probe, upon reaching a second time that is subsequent to the first time by a predetermined delay period, the one or more echo signals from the needle; and b-ii) generating, by the ultrasound scanner, needle tip image data corresponding to a location of a tip of the needle based on the one or more echo signals; c) performing, by the scanner, a tissue detection process, the tissue detection process comprising: c-i) receiving, at the imaging probe, the one or more echo signals from the adjacent tissue; and c-ii) generating, by the scanner, tissue image data corresponding to the adjacent tissue based on the one or more echo signals; d) generating, by the ultrasound scanner, a compound image that includes a visual indicator of the location of the needle tip with respect to the tissue based on the needle tip image data and the tissue image data, wherein the visual indicator of the location of the needle tip is a double ringdown artifact that comprises: a top ringdown artifact propagating from the location of the needle tip towards the top of the compound image; and a bottom ringdown artifact propagating from the location of the needle tip towards the bottom of the compound image; and e) displaying, by the ultrasound scanner, the compound image on a display.

12. The method of claim 11, wherein, in the needle tip detection process, the one or more echo signals from the needle are not received between the first time and the second time.

13. The method of claim 11, wherein a narrowest point of the top ringdown artifact and a narrowest point of the bottom ringdown artifact each correspond to the location of the needle tip.

14. The method of claim 11, wherein the predetermined delay period is a value within a range of 40 to 500 microseconds.

15. The method of claim 11, wherein the predetermined delay period is a value within a range of 100 to 400 microseconds.

16. The method of claim 11, wherein the predetermined delay period is relatively short such that one or more echo signals from the adjacent tissue partly obscure the double ringdown artifact, and wherein an appearance of the one or more echo signals from the adjacent tissue in the compound image is removed using signal processing.

17. The method of claim 11, wherein the needle tip detection process comprises applying a gain to the one or more echo signals received from the needle that is greater than any gain applied to the one or more echo signals received from the adjacent tissue in the tissue detection process.

18. The method of claim 11, wherein, for the needle tip detection process:

the one or more ultrasonic pulse signals are focused pulse signals; and at least one of the elements a), or b-i), is repeated one or more times.

19. The method of claim 11, wherein the needle tip detection process is repeated one or more times before carrying out the tissue detection process, wherein the needle tip image radiofrequency data is accumulated and averaged, and wherein the generation of the compound image is based on the accumulated and averaged needle tip image radiofrequency data.

20. The method of claim 11, wherein during the predetermined delay period the one or more echo signals produced by the adjacent tissue dissipate and the one or more echo signals produced by the needle persist.

* * * * *